United States Patent
Pulé et al.

(10) Patent No.: US 10,954,530 B2
(45) Date of Patent: Mar. 23, 2021

(54) RETROVIRAL AND LENTIVIRAL VECTORS

(71) Applicant: AUTOLUS LIMITED, London (GB)

(72) Inventors: Martin Pulé, London (GB); Leila Mekkaoui, London (GB)

(73) Assignee: AUTOLUS LIMITED, London (GB)

( * ) Notice: Subject to any disclaimer, the term of this patent is extended or adjusted under 35 U.S.C. 154(b) by 687 days.

(21) Appl. No.: 15/554,499

(22) PCT Filed: Mar. 1, 2016

(86) PCT No.: PCT/GB2016/050537
§ 371 (c)(1),
(2) Date: Aug. 30, 2017

(87) PCT Pub. No.: WO2016/139463
PCT Pub. Date: Sep. 9, 2016

(65) Prior Publication Data
US 2018/0066280 A1 Mar. 8, 2018

(30) Foreign Application Priority Data

Mar. 2, 2015 (GB) ..................................... 1503500

(51) Int. Cl.
| | | |
|---|---|---|
| *A61K 39/00* | (2006.01) | |
| *A61K 35/17* | (2015.01) | |
| *C12N 5/0783* | (2010.01) | |
| *A61K 35/12* | (2015.01) | |
| *A61K 48/00* | (2006.01) | |
| *C12N 15/86* | (2006.01) | |
| *C07K 14/725* | (2006.01) | |
| *C07K 16/28* | (2006.01) | |
| *A61K 35/76* | (2015.01) | |
| *A61K 38/00* | (2006.01) | |
| *C07K 16/00* | (2006.01) | |
| *C07K 14/00* | (2006.01) | |

(52) U.S. Cl.
CPC .............. *C12N 15/86* (2013.01); *A61K 35/76* (2013.01); *A61K 38/00* (2013.01); *C07K 14/00* (2013.01); *C07K 14/7051* (2013.01); *C07K 16/00* (2013.01); *C07K 16/2809* (2013.01); *C07K 16/2818* (2013.01); *A61K 2039/507* (2013.01); *C07K 2317/622* (2013.01); *C07K 2317/75* (2013.01); *C12N 2740/13032* (2013.01); *C12N 2740/13045* (2013.01); *C12N 2740/13052* (2013.01); *C12N 2740/15032* (2013.01); *C12N 2740/15045* (2013.01); *C12N 2740/15052* (2013.01); *C12N 2810/852* (2013.01); *C12N 2810/855* (2013.01); *C12N 2810/859* (2013.01)

(58) Field of Classification Search
CPC .......... A61P 35/00; A61P 37/06; A61K 35/17; A61K 48/00; A61K 39/0011
See application file for complete search history.

(56) References Cited

U.S. PATENT DOCUMENTS

| 2017/0240920 A1 | 8/2017 | Pulé et al. |
| 2019/0177746 A1 | 6/2019 | Peddareddigari et al. |

FOREIGN PATENT DOCUMENTS

| WO | WO-97/05266 A1 | 2/1997 |
| WO | WO-2004/080404 A2 | 9/2004 |
| WO | WO-2006/007539 A1 | 1/2006 |
| WO | WO2006007539 * | 1/2006 |
| WO | WO-2007/095201 A2 | 8/2007 |
| WO | WO-2009/014726 A1 | 1/2009 |
| WO | WO2011067553 * | 1/2009 |
| WO | WO-2011/067553 A1 | 6/2011 |
| WO | WO-2013/153391 A1 | 10/2013 |
| WO | WO-2018/033726 A1 | 2/2018 |

OTHER PUBLICATIONS

International Search Report and Written Opinion from International Application No. PCT/GB2016/050537 dated Aug. 9, 2016.
Schaffer et al., "Molecular Engineering of Viral Gene Delivery Vehicles," Annu. Rev. Biomed. Eng. 10:169-94 (2008).
Verhoeyen et al., "Lentiviral Vector Gene Transfer into Human T Cells," Method in Molecular Biology 506:97-114(2009).
Verhoeyen et al., "Surface-engineering of lentiviral vectors," J Gene Med 6:S83-S94 (2004).
U.S. Appl. No. 15/506,391 (US-2017-0240920), filed Feb. 24, 2017.
U.S. Appl. No. 16/326,131 (US-2019-0177746), filed Feb. 15, 2019.
Li et al., Mimotope vaccination for epitope-specific induction of anti-CD20 antibodies. *Cell Immunol.* 239: 136-43 (2006).
Maurice et al., Efficient gene transfer into human primary blood lymphocytes by surface-engineered lentiviral vectors that display a T cell-activating polypeptide. *Blood*, 99: 2342-50 (2002).
Morizono et al., A versatile targeting system with lentiviral vectors bearing the biotin-adaptor peptide. *J. Gene Med.* 11: 655-63 (2009).
Perosa et al., Identification of an antigenic and immunogenic motif expressed by two 7-mer rituximab-specific cyclic peptide mimotopes: implication for peptide-based active immunotherapy. *J. Immunol.* 179: 7967-74 (2007).
Udomsinprasert et al., Identification, characterization and structure of a new Delta class glutathione transferase isoenzyme. *Biochem. J.* 388 (Pt 3): 763-71 (2005).

(Continued)

Primary Examiner — Barry A Chestnut
(74) Attorney, Agent, or Firm — Marshall, Gerstein & Borun LLP

(57) ABSTRACT

The present invention provides a retroviral or lentiviral vector having a viral envelope which comprises: (i) a mitogenic T-cell activating transmembrane protein which comprises a mitogenic domain and a transmembrane domain; and/or (ii) a cytokine-based T-cell activating transmembrane protein which comprises a cytokine domain and a transmembrane domain, wherein the mitogenic or cytokine-based T-cell activating transmembrane protein is not part of a viral envelope glycoprotein. When cells such as T-cells of Natural Killer cells are transduced by such a viral vector, they are simultaneously activated by the mitogenic T-cell activating transmembrane protein and/or the cytokine-based T-cell activating transmembrane protein.

12 Claims, 11 Drawing Sheets

Specification includes a Sequence Listing.

(56) References Cited

OTHER PUBLICATIONS

Verhoeyen et al., IL-7 surface-engineered lentiviral vectors promote survival and efficient gene transfer in resting primary T lymphocytes. *Blood*, 101: 2167-74 (2003).
Yang et al., Cell type-specific targeting with surface-engineered lentiviral vectors co-displaying OKT3 antibody and fusogenic molecule. *Pharm. Res.* 26: 1432-45 (2009).
Ye et al., Tagging retrovirus vectors with a metal binding peptide and one-step purification by immobilized metal affinity chromatography. *J. Virol.* 78: 9820-7 (2004).

* cited by examiner

RETROVIRAL AND LENTIVIRAL VECTORS

The present invention relates to retroviral and lentiviral vectors and cells for their production. The vectors may be used for transducing cells, such as T-cells. In particular, the invention relates retroviral or lentiviral vectors capable of both transducing and activating a cell, such as a T cell.

BACKGROUND TO THE INVENTION

The generation of engineered T-cell products typically requires stimulation with a mitogen followed by transduction with an integrating vector, such as a lentiviral vector or a retroviral vector.

A widely used approach is to add soluble mitogenic monoclonal antibodies (mAb), such as anti-TCR/CD3 and anti-CD28, to the cell culture. An alternative approach is to attach anti-TCR/CD3 mAb along with anti-CD28 mAb to a bead. The surface of the bead has improved T cell activating properties compared to the soluble antibodies alone.

In addition cytokines (e.g. IL2, IL15 or IL7) are commonly added to the cell culture.

These mitogen antibodies and cytokines are single-use consumables and typically represent the most costly part of the T-cell production process.

Maurice et al. describe the direct engineering of a lentiviral envelope protein such that the CD3 agonist OKT3 is displayed on the virion surface (Maurice et al.; Blood; 2002; 99; 2342-2350). Verhoeyen et al. describe a similar approach in which the lentiviral envelope protein is engineered to incorporate IL7 (Verhoeyen et al.; Blood; 2003; 101; 2167-2174).

Each of these engineering approaches requires complex engineering of the viral envelope protein. This complex engineering must be performed for each discrete peptide to be displayed on the virion surface. The approach has also been shown to reduce viral titre.

There is thus a need for new approaches for generating engineered T cell products which are not associated with the disadvantages described above.

SUMMARY OF ASPECTS OF THE INVENTION

Figure 1:
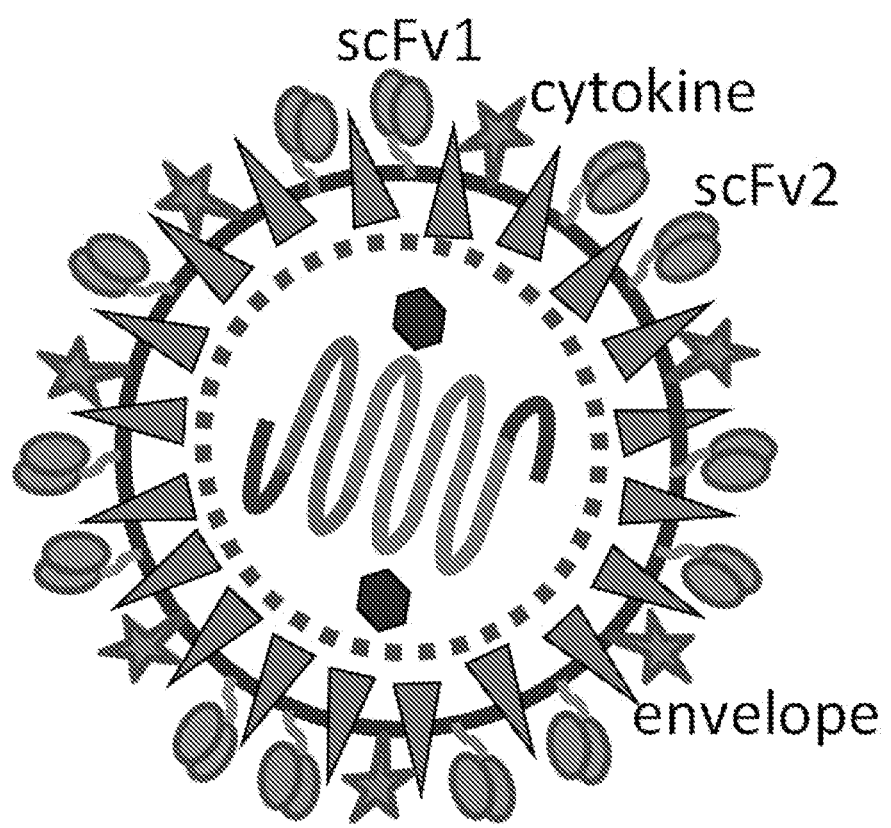
FIG. 1—Diagram of a retroSTIM vector surrounded by a lipid bilayer which is studded with the RD114 envelope glycoprotein and various mitogenic elements such as scFv or membrane-bound cytokines.

The present invention is based on the finding that it is possible to incorporate a mitogenic stimulus, and/or a cytokine stimulus, into a retroviral or lentiviral capsid, such that the virus both activates and transduces T cells. This removes the need to add vector, mitogen and cytokines. The invention involves including a mitogenic transmembrane protein and/or a cytokine-based transmembrane protein in the producer or packaging cell, which get(s) incorporated into the retrovirus when it buds from the producer/packaging cell membrane. The mitogenic transmembrane protein and/or a cytokine-based transmembrane protein is/are expressed as a separate cell surface molecule on the producer cell rather than being part of the viral envelope glycoprotein. This means that the reading frame of the viral envelope is unaffected, which therefore preserves functional integrity and viral titre.

Thus in a first aspect the present invention provides a retroviral or lentiviral vector having a viral envelope which comprises:
(i) a mitogenic T-cell activating transmembrane protein which comprises a mitogenic domain and a transmembrane domain; and/or
(ii) a cytokine-based T-cell activating transmembrane protein which comprises a cytokine domain and a transmembrane domain
wherein the mitogenic or cytokine-based T-cell activating transmembrane protein is not part of a viral envelope glycoprotein The retroviral or lentiviral vector may comprise a separate viral envelope glycoprotein, encoded by an env gene.

Thus there is provided a retroviral or lentiviral vector having a viral envelope which comprises:
(i) a viral envelope glycoprotein: and
(ii) a mitogenic T-cell activating transmembrane protein having the structure:

M-S-TM in which M is a mitogenic domain; S is an optional spacer and TM is a transmembrane domain; and/or
(iii) a cytokine-based T-cell activating transmembrane protein which comprises a cytokine domain and a transmembrane domain.

The mitogenic T-cell activating transmembrane protein and/or cytokine-based T-cell activating transmembrane protein are not part of the viral envelope glycoprotein. They exist as separate proteins in the viral envelope and are encoded by separate genes.

The mitogenic T-cell activating transmembrane protein may have the structure:

M-S-TM in which M is a mitogenic domain; S is an optional spacer and TM is a transmembrane domain.

The mitogenic T-cell activating transmembrane protein may bind an activating T-cell surface antigen such as CD3, CD28, CD134 or CD137. The mitogenic T-cell activating transmembrane protein may comprise an agonist for such an activating T-cell surface antigen.

The mitogenic T-cell activating transmembrane protein may comprise the binding domain from an antibody such as OKT3, 15E8, TGN1412; or a costimulatory molecule such as OX40L or 41BBL.

The viral vector may comprise two or more mitogenic T-cell activating transmembrane proteins in the viral envelope. For example, the viral vector may comprise a first mitogenic T-cell activating transmembrane protein which binds CD3 and a second mitogenic T-cell activating transmembrane protein which binds CD28.

The cytokine-based T-cell activating transmembrane protein may, for example, comprise a cytokine selected from IL2, IL7 and IL15.

In particular there is provided a retroviral or lentiviral vector having a viral envelope which comprises:
(ia) a first mitogenic T-cell activating transmembrane protein which binds CD3; and
(ib) a second mitogenic T-cell activating transmembrane protein which binds CD28.

There is also provided a retroviral or lentiviral vector having a viral envelope which comprises:
(ia) a first mitogenic T-cell activating transmembrane protein which binds CD3;
(ib) a second mitogenic T-cell activating transmembrane protein which binds CD28; and
(ii) a cytokine-based T-cell activating transmembrane protein which comprises IL2.

There is also provided a retroviral or lentiviral vector having a viral envelope which comprises:
(ia) a first mitogenic T-cell activating transmembrane protein which binds CD3;
(ib) a second mitogenic T-cell activating transmembrane protein which binds CD28;
(iia) a cytokine-based T-cell activating transmembrane protein which comprises IL7; and
(iib) a cytokine-based T-cell activating transmembrane protein which comprises IL15.

The viral vector may comprise a heterologous viral envelope glycoprotein giving a pseudotyped viral vector. For example, the viral envelope glycoprotein may be derived from RD114 or one of its variants, VSV-G, Gibbon-ape leukaemia virus (GALV), or is the Amphotropic envelope, Measles envelope or baboon retroviral envelope glycoprotein.

In a second embodiment of the first aspect of the invention, the viral envelope of the viral vector may also comprise:
(iv) a tagging protein which comprises:
a binding domain which binds to a capture moiety
a spacer; and
a transmembrane domain
which tagging protein facilitates purification of the viral vector from cellular supernatant via binding of the tagging protein to the capture moiety.

The binding domain of the tagging protein may comprise one or more streptavidin-binding epitope(s). The streptavidin-binding epitope(s) may be a biotin mimic, such as a biotin mimic which binds streptavidin with a lower affinity than biotin, so that biotin may be used to elute streptavidin-captured retroviral vectors produced by the packaging cell.

Examples of suitable biotin mimics include: StreptagII (SEQ ID NO: 36), Flankedccstretag (SEQ ID NO: 37) and ccstreptag (SEQ ID NO:38).

The viral vector of the first aspect of the invention may comprise a nucleic acid sequence encoding a T-cell receptor or a chimeric antigen receptor.

The viral vector may be a virus-like particle (VLP).

In a second aspect, the present invention provides a host cell which expresses, at the cell surface,
(ii) a mitogenic T-cell activating transmembrane protein comprising a mitogenic domain and a transmembrane domain; and/or
(ii) a cytokine-based T-cell activating transmembrane protein which comprises a cytokine domain and a transmembrane domain
such that a retroviral or lentiviral vector produced by the packaging cell is as defined in the first aspect of the invention.

In a second embodiment of the second aspect of the invention, the host cell may also express, at the cell surface:
(iii) a tagging protein which comprises:
a binding domain which binds to a capture moiety; and
a transmembrane domain
which tagging protein facilitates purification of the viral vector from cellular supernatant via binding of the tagging protein to the capture moiety, such that a retroviral or lentiviral vector produced by the packaging cell is as defined in the second embodiment of the first aspect of the invention.

The tagging protein may also comprise a spacer between the binding domain and the transmembrane domain.

The term host cell may be a packaging cell or a producer cell.

A packaging cell may comprise one or more of the following genes: gag, pol, env and/or rev.

A producer cell comprises gag, pol, env and optionally rev genes and also comprises a retroviral or lentiviral genome.

In this respect, the host cell may be any suitable cell line stably expressing mitogenic and/or cytokine transmembrane proteins. It may be transiently transfected with transfer vector, gagpol, env (and rev in the case of a lentivirus) to produce replication incompetent retroviral/lentiviral vector.

In a third aspect there is provided a method for making a host cell according to the second aspect of the invention, which comprises the step of transducing or transfecting a cell with a nucleic acid encoding a mitogenic T-cell activating transmembrane protein and/or a cytokine-based T-cell activating transmembrane protein.

In a fourth aspect there is provided a method for producing a viral vector according to the first aspect of the invention which comprises the step of expressing a retroviral or lentiviral genome in a cell according to the second aspect of the invention.

In a fifth aspect, there is provided a method for making an activated transgenic T-cell or natural killer (NK) cell, which comprises the step of transducing a T or NK cell with a viral vector according to the first aspect of the invention, such that the T-cell or NK cell is activated by the one or more mitogenic T-cell activating transmembrane protein(s) and/or the one or more cytokine-based T-cell activating transmembrane protein(s).

In a sixth aspect, there is provided a kit for making a retroviral or lentiviral vector as defined in the first aspect of the invention, which comprises:
(i) a host cell as defined in the second aspect of the invention;
(ii) nucleic acids comprising gag,pol,env and optionally rev; and
(iii) a retroviral genome.

There is also provided is provided a kit for making a retroviral or lentiviral vector as defined in the first aspect of the invention, which comprises:
(i) a packaging cell as defined in the second aspect of the invention; and
(ii) a retroviral genome.

There is also provided a kit for making a packaging cell according to the second embodiment of the second aspect of the invention which comprises:
(i) one or more nucleic acid(s) encoding a mitogenic T-cell activating transmembrane protein and/or a cytokine-based T-cell activating transmembrane protein; and
(ii) nucleic acids comprising retroviral gag, pol and env genes.

There is also provided a kit for making a producer cell according to the second aspect of the invention, which comprises:
(i) one or more nucleic acid(s) encoding a mitogenic T-cell activating transmembrane protein and/or a cytokine-based T-cell activating transmembrane protein;
(ii) nucleic acids comprising retroviral gag, pol and env genes; and
(iii) a retroviral or lentiviral vector genome The invention therefore provides a viral vector with a built-in mitogenic stimulus and/or cytokine stimulus (see FIG. 1). The vector has the capability to both stimulate the T-cell and to also effect gene insertion. This has a number of advantages: (1) it simplifies the process of T-cell engineering, as only one component needs to be added; (2) it avoids removal of beads and the associated reduction in yield as the virus is labile and does not have to be removed. (3) it reduces the cost of T-cell engineering as only one component needs to be manufactured; (4) it allows greater design flexibility: each T-cell engineering process will involve making a gene-transfer vector, the same product can also be made with a mitogenic stimulus to "fit" the product; (5) it allows for a shortened production process: in soluble antigen/bead-based approaches the mitogen and the vector are typically given sequentially separated by one, two or sometimes three days, this can be avoided with the retroviral vector of the present invention since mitogenic stimulation and viral entry are synchronized and simultaneous; (6) it is easier to engineer as there is no need to test a lot of different fusion proteins for expression and functionality; (7) it is possible to add more than one signal at the same time; and (8) it is possible to regulate the expression and/or expression levels of each signal/protein separately.

Since the mitogenic stimulus and/or cytokine stimulus are provided on a molecule which is separate from the viral envelope glycoprotein, integrity of the viral envelope glycoprotein is maintained and there is no negative impact on viral titre.

DETAILED DESCRIPTION

Retroviruses

Retroviruses are double stranded RNA enveloped viruses mainly characterized by the ability to "reverse-transcribe" their genome from RNA to DNA. Virions measure 100-120 nm in diameter and contain a dimeric genome of identical positive RNA strands complexed with the nucleocapsid proteins. The genome is enclosed in a proteic capsid that also contains enzymatic proteins, namely the reverse transcriptase, the integrase and proteases, required for viral infection. The matrix proteins form a layer outside the capsid core that interacts with the envelope, a lipid bilayer derived from the host cellular membrane, which surrounds the viral core particle. Anchored on this bilayer, are the viral envelope glycoproteins responsible for recognizing specific receptors on the host cell and initiating the infection process. Envelope proteins are formed by two subunits, the transmembrane (TM) that anchors the protein into the lipid membrane and the surface (SU) which binds to the cellular receptors.

Based on the genome structure, retroviruses are classified into simple retroviruses, such as MLV and murine leukemia virus; or complex retroviruses, such as HIV and EIAV. Retroviruses encode four genes: gag (group specific antigen), pro (protease), pol (polymerase) and env (envelope). The gag sequence encodes the three main structural proteins: the matrix protein, nucleocapsid proteins, and capsid protein. The pro sequence encodes proteases responsible for cleaving Gag and Gag-Pol during particle assembly, budding and maturation. The pol sequence encodes the enzymes reverse transcriptase and integrase, the former catalyzing the reverse transcription of the viral genome from RNA to DNA during the infection process and the latter responsible for integrating the proviral DNA into the host cell genome. The env sequence encodes for both SU and TM subunits of the envelope glycoprotein. Additionally, retroviral genome presents non-coding cis-acting sequences such as: two LTRs (long terminal repeats), which contain elements required to drive gene expression, reverse transcription and integration into the host cell chromosome; a sequence named packaging signal (ψ) required for specific packaging of the viral RNA into newly forming virions; and a polypurine tract (PPT) that functions as the site for initiating the positive strand DNA synthesis during reverse transcription. In addition to gag, pro, pol and env, complex retroviruses, such as lentiviruses, have accessory genes including vif, vpr, vpu, nef, tat and rev that regulate viral gene expression, assembly of infectious particles and modulate viral replication in infected cells.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process known as "budding".

When enveloped viruses, such as retrovirus and lentivirus, bud out of the host cells, they take part of the host cell lipidic membrane. In this way, host-cell derived membrane proteins become part of the retroviral particle. The present invention utilises this process in order to introduce proteins of interest into the envelope of the viral particle.

Retroviral Vectors

Retroviruses and lentiviruses may be used as a vector or delivery system for the transfer of a nucleotide of interest (NOI), or a plurality of NOIs, to a target cell. The transfer can occur in vitro, ex vivo or in vivo. When used in this fashion, the viruses are typically called viral vectors.

In the viral vectors of the present invention, the NOI may encode a T cell receptor or a chimeric antigen receptor and/or a suicide gene.

Gamma-retroviral vectors, commonly designated retroviral vectors, were the first viral vector employed in gene therapy clinical trials in 1990 and are still one of the most used. More recently, the interest in lentiviral vectors, derived from complex retroviruses such as the human immunodeficiency virus (HIV), has grown due to their ability to transduce non-dividing cells. The most attractive features of retroviral and lentiviral vectors as gene transfer tools include the capacity for large genetic payload (up to 9 kb), minimal patient immune response, high transducing efficiency in vivo and in vitro, and the ability to permanently modify the genetic content of the target cell, sustaining a long-term expression of the delivered gene.

The retroviral vector can be based on any suitable retrovirus which is able to deliver genetic information to eukaryotic cells. For example, the retroviral vector may be an alpharetroviral vector, a gammaretroviral vector, a lentiviral vector or a spumaretroviral vector. Such vectors have been used extensively in gene therapy treatments and other gene delivery applications.

The viral vector of the present invention may be a retroviral vector, such as a gamma-retroviral vector. The viral vector may be based on human immunodeficiency virus.

The viral vector of the present invention may be a lentiviral vector. The vector may be based on a non-primate lentivirus such as equine infectious anemia virus (EIAV).

The viral vector of the invention comprises a mitogenic T-cell activating transmembrane protein and/or a cytokine-based T-cell activating transmembrane protein in the viral envelope, as illustrated in FIG. 1.

The mitogenic T-cell activating transmembrane protein and/or cytokine-based T-cell activating transmembrane protein is/are derived from the host cell membrane, as explained above.

Virus-Like Particles (VLPs)

For retroviral and lentiviral vectors, the expression of the Gag precursor is sufficient to mediate virion assembly and release. Gag proteins, and even fragments of Gag, have been shown competent to assemble in vitro to form various structures that resemble virion cores. These particles that are devoid of viral genetic material, and are hence non-infectious, are called virus-like particles (VLPs). Like with complete viral particles they contain an outer viral envelope made of the host cell lipid-bi-layer (membrane), and hence contain host cell transmembrane proteins.

The viral vector of the first aspect of the invention may be or comprise a virus-like particle.

Nucleotide of Interest (NOI)

The viral vector of the present invention is capable of delivering a nucleotide of interest (NOI) to a target cell, such as a T cell or a natural killer (NK) cell.

The NOI may encode all or part of a T-cell receptor (TCR) or a chimeric antigen receptor (CAR) and/or a suicide gene.

CARs, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A trans-membrane domain anchors the protein in the cell membrane. A CAR may comprise or associate with an intracellular T-cell signalling domain or endodomain.

CAR-encoding nucleic acids may be transferred to cells, such a T cells, using the retroviral or lentiviral vector of the present invention. In this way, a large number of cancer-specific T cells can be generated for adoptive cell transfer. When the CAR binds the target-antigen, this results in the transmission of an activating signal to the T-cell it is expressed on. Thus the CAR directs the specificity and cytotoxicity of the T cell towards tumour cells expressing the targeted antigen.

A suicide gene encodes a polypeptide which enable the cells expressing such a polypeptide to be deleted, for example by triggering apoptosis. An example of a suicide gene is described in WO2013/153391.

Host Cell

In a second aspect, the invention provides a host cell which expresses a mitogenic T-cell activating transmembrane protein or a cytokine-based T-cell activating transmembrane protein at the cell surface.

The host cell may be for the production of viral vectors according to the first aspect of the invention.

The host cell may be a packaging cell and comprise one or more of the following genes: gag, pol, env and rev.

A packaging cell for a retroviral vector may comprise gag, pol and env genes. A packaging cell for a lentiviral vector may comprises gag, pol, env and rev genes.

The host cell may be a producer cell and comprise gag, pol, env and optionally rev genes and a retroviral or lentiviral vector genome.

In a typical recombinant retroviral or lentiviral vector for use in gene therapy, at least part of one or more of the gag-pol and env protein coding regions may be removed from the virus and provided by the packaging cell. This makes the viral vector replication-defective as the virus is capable of integrating its genome into a host genome but the modified viral genome is unable to propagate itself due to a lack of structural proteins.

Packaging cells are used to propagate and isolate quantities of viral vectors i.e to prepare suitable titres of the retroviral vector for transduction of a target cell.

In some instances, propagation and isolation may entail isolation of the retroviral gagpol and env (and in the case of lentivirus, rev) genes and their separate introduction into a host cell to produce a packaging cell line. The packaging cell line produces the proteins required for packaging retroviral DNA but it cannot bring about encapsidation due to the lack of a psi region. However, when a recombinant vector carrying a psi region is introduced into the packaging cell line, the helper proteins can package the psi-positive recombinant vector to produce the recombinant virus stock.

A summary of the available packaging lines is presented in "Retroviruses" (1997 Cold Spring Harbour Laboratory Press Eds: J M Coffin, S M Hughes, H E Varmus pp 449).

Packaging cells have also been developed in which the gag, pol and env (and, in the case of lentiviral vectors, rev) viral coding regions are carried on separate expression plasmids that are independently transfected into a packaging cell line, so that three recombinant events are required for wild type viral production.

Transient transfection avoids the longer time required to generate stable vector-producing cell lines and is used if the vector or retroviral packaging components are toxic to cells. Components typically used to generate retroviral/lentivial vectors include a plasmid encoding the Gag/Pol proteins, a plasmid encoding the Env protein (and, in the case of lentiviral vectors, the rev protein), and the retroviral/lentiviral vector genome. Vector production involves transient transfection of one or more of these components into cells containing the other required components.

The packaging cells of the present invention may be any mammalian cell type capable of producing retroviral/lentiviral vector particles. The packaging cells may be 293T-cells, or variants of 293T-cells which have been adapted to grow in suspension and grow without serum.

The packaging cells may be made by transient transfection with
a) the transfer vector
b) a gagpol expression vector
c) an env expression vector. The env gene may be a heterologous, resulting in a pseudotyped retroviral vector. For example, the env gene may be from RD114 or one of its variants, VSV-G, the Gibbon-ape leukaemia virus (GALV), the Amphotropic envelope or Measles envelope or baboon retroviral envelope glycoprotein.

In the case of lentiviral vector, transient transfection with a rev vector is also performed.

Mitogenic T-Cell Activating Transmembrane Protein

The viral vector of the present invention may comprise a mitogenic T-cell activating transmembrane protein in the viral envelope. The mitogenic T-cell activating transmembrane protein is derived from the host cell during retroviral vector production. The mitogenic T-cell activating transmembrane protein is made by the packaging cell and expressed at the cell surface. When the nascent retroviral vector buds from the host cell membrane, the mitogenic T-cell activating transmembrane protein is incorporated in the viral envelope as part of the packaging cell-derived lipid bilayer.

The term "host-cell derived" indicates that the mitogenic T-cell activating transmembrane protein is derived from the host cell as described above and is not produced as a fusion or chimera from one of the viral genes, such as gag, which encodes the main structural proteins; or env, which encodes the envelope protein.

Envelope proteins are formed by two subunits, the transmembrane (TM) that anchors the protein into the lipid membrane and the surface (SU) which binds to the cellular receptors. The packaging-cell derived mitogenic T-cell activating transmembrane protein of the present invention does not comprise the surface envelope subunit (SU).

The mitogenic T-cell activating transmembrane protein may comprise one of the following sequences, or a variant thereof.

(OKT3-CD8STK-TM-A)
SEQ ID No. 1
METDTLLLWVLLLWVPGSTGQVQLQQSGAELARPGASVKMSCKASGYTFT

RYTMHWVKQRPGQGLEWIGYINPSRGYTNYNQKFKDKATLTTDKSSSTAY

MQLSSLTSEDSAVYYCARYYDDHYCLDYWGQGTTLTVSSSGGGGSGGGGS

GGGGSQIVLTQSPAIMSASPGEKVTMTCSASSSVSYMNWYQQKSGTSPKR

WIYDTSKLASGVPAHFRGSGSGTSYSLTISGMEAEDAATYYCQQWSSNPF

TFGSGTKLEINRSDPTTTPAPRPPTPAPTIASQPLSLRPEACRPAAGGAV

HTRGLDFACDIYIWAPLAGTCGVLLLSLVITLYCNHRNRRRVCKCPRPVV (15E8-CD8STK-TM-A)
SEQ ID No. 2
METDTLILWVLLLLVPGSTGQVQLKESGPGLVAPSQSLSITCTVSGFSLT

SYGVHWVRQPPGKGLEWLGVIWAGGSTNYNSALMSRLSISKDNSKSQVFL

KMNSLQTDDTAMYYCARDKRAPGKLYYGYPDYWGQGTTLTVSSGGGGSGG

GGSGGGGSDIVLTQSPASLAVSLGQRATISCRASESVEYYVTSLMQWYQQ

KPGQPPKLLIYAASNVESGVPARFSGSGSGTDFSLNIHPVEEDDIAMYFC

QQTRKVPSTFGGGTKLEIKRSDPTTTPAPRPPTPAPTIASQPLSLRPEAC

RPAAGGAVHTRGLDFACDIYIWAPLAGTCGVLLLSLVITLYCNHRNRRRV

CKCPRPVV (TGN1412-CD8STK-TM-A)
SEQ ID No. 3
METDTLILWVLLLLVPGSTGQVQLVQSGAEVKKPGASVKVSCKASGYTF

TSYYIHWVRQAPGQGLEWIGCIYPGNVNTNYNEKFKDRATLTVDTSIST

AYMELSRLRSDDTAVYFCTRSHYGLDWNFDVWGQGTTVTVSSGGGGSGG

GGSGGGGSDIQMTQSPSSLSASVGDRVTITCHASQNIYVWLNWYQQKPG

KAPKLLIYKASNLHTGVPSRFSGSGSGTDFTLTISSLQPEDFATYYCQQ

GQTYPYTFGGGTKVEIKRSDPTTTPAPRPPTPAPTIASQPLSLRPEACR

PAAGGAVHTRGLDFACDIYIWAPLAGTCGVLLLSLVITLYCNHRNRRRV

CKCPRPVV

The mitogenic T-cell activating transmembrane protein may comprise a variant of the sequence shown as SEQ ID No. 1, 2 or 3 having at least 80, 85, 90, 95, 98 or 99% sequence identity, provided that the variant sequence is a mitogenic T-cell activating transmembrane protein having the required properties i.e. the capacity to activate a T cell when present in the envelope protein of a retroviral vector.

Methods of sequence alignment are well known in the art and are accomplished using suitable alignment programs. The % sequence identity refers to the percentage of amino acid or nucleotide residues that are identical in the two sequences when they are optimally aligned. Nucleotide and protein sequence homology or identity may be determined using standard algorithms such as a BLAST program (Basic Local Alignment Search Tool at the National Center for Biotechnology Information) using default parameters, which is publicly available at blast.ncbi.nlm.nih.gov. Other algorithms for determining sequence identity or homology include:

LALIGN (ebi.ac.uk/Tools/psa/lalign/and ebi.ac.uk/Tools/psailaligninucleotide.html), AMAS (Analysis of Multiply Aligned Sequences, at compbio.dundee.ac.uk/Software/Amas/amas.html), FASTA (ebi.ac.uk/Tools/sss/fasta/), Clustal Omega (ebi.ac.uk/Tools/msa/clustalo/), SIM web.expasy.orgisim/), and EMBOSS Needle (ebi.ac.uk/Tools/psa/emboss needleinucleotide.html).

The mitogenic T-cell activating transmembrane protein may have the structure:

M-S-TM in which M is a mitogenic domain; S is an optional spacer domain and TM is a transmembrane domain.

Mitogenic Domain

The mitogenic domain is the part of the mitogenic T-cell activating transmembrane protein which causes T-cell activation. It may bind or otherwise interact, directly or indirectly, with a T cell, leading to T cell activation. In particular, the mitogenic domain may bind a T cell surface antigen, such as CD3, CD28, CD134 and CD137.

CD3 is a T-cell co-receptor. It is a protein complex composed of four distinct chains. In mammals, the complex contains a CD3γ chain, a CD3δ chain, and two CD3ε chains. These chains associate with the T-cell receptor (TCR) and the ζ-chain to generate an activation signal in T lymphocytes. The TCR, ζ-chain, and CD3 molecules together comprise the TCR complex.

The mitogenic domain may bind to CD3 ε chain.

CD28 is one of the proteins expressed on T cells that provide co-stimulatory signals required for T cell activation and survival. T cell stimulation through CD28 in addition to the T-cell receptor (TCR) can provide a potent signal for the production of various interleukins (IL-6 in particular).

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels.

CD137, also known as 4-1BB, is a member of the tumor necrosis factor (TNF) receptor family. CD137 can be expressed by activated T cells, but to a larger extent on CD8 than on CD4 T cells. In addition, CD137 expression is found on dendritic cells, follicular dendritic cells, natural killer cells, granulocytes and cells of blood vessel walls at sites of inflammation. The best characterized activity of CD137 is its costimulatory activity for activated T cells. Crosslinking of CD137 enhances T cell proliferation, IL-2 secretion survival and cytolytic activity.

The mitogenic domain may comprise all or part of an antibody or other molecule which specifically binds a T-cell surface antigen. The antibody may activate the TCR or CD28. The antibody may bind the TCR, CD3 or CD28. Examples of such antibodies include: OKT3, 15E8 and TGN1412. Other suitable antibodies include:

Anti-CD28: CD28.2, 10F3

Anti-CD3/TCR: UCHT1, YTH12.5, TR66

The mitogenic domain may comprise the binding domain from OKT3, 15E8, TGN1412, CD28.2, 10F3, UCHT1, YTH12.5 or TR66.

The mitogenic domain may comprise all or part of a co-stimulatory molecule such as OX40L and 41BBL. For example, the mitogenic domain may comprise the binding domain from OX40L or 41BBL.

OKT3, also known as Muromonab-CD3 is a monoclonal antibody targeted at the CD3ε chain. It is clinically used to reduce acute rejection in patients with organ transplants. It was the first monoclonal antibody to be approved for clinical use in humans. The CDRs of OKT3 are as follows

| | | |
|---|---|---|
| CDRH1: | GYTFTRY | (SEQ ID No. 4) |
| CDRH2: | NPSRGY | (SEQ ID No. 5) |
| CDRH3: | YYDDHYCLDY | (SEQ ID No. 6) |
| CDRL1: | SASSSVSYMN | (SEQ ID No. 7) |
| CDRL2: | DTSKLAS | (SEQ ID No. 8) |
| CDRL3: | QQWSSNPFT | (SEQ ID No. 9) |

15E8 is a mouse monoclonal antibody to human CD28. Its CDRs are as follows:

| | | |
|---|---|---|
| CDRH1: | GFSLTSY | (SEQ ID No. 10) |
| CDRH2: | WAGGS | (SEQ ID No. 11) |
| CDRH3: | DKRAPGKLYYGYPDY | (SEQ ID No. 12) |
| CDRL1: | RASESVEYYVTSLMQ | (SEQ ID No. 13) |
| CDRL2: | AASNVES | (SEQ ID No. 14) |
| CDRL3: | QQTRKVPST | (SEQ ID No. 15) |

TGN1412 (also known as CD28-SuperMAB) is a humanised monoclonal antibody that not only binds to, but is a strong agonist for, the CD28 receptor. Its CDRs are as follows.

| | | |
|---|---|---|
| CDRH1: | GYTFSY | (SEQ ID No. 16) |
| CDRH2: | YPGNVN | (SEQ ID No. 17) |
| CDRH3: | SHYGLDWNFDV | (SEQ ID No. 18) |

```
                                     (SEQ ID No. 19)
CDRL1:              HASQNIYVLN (SEQ ID No. 20)
CDRL2:              KASNLHT (SEQ ID No. 21)
CDRL3:              QQGQTYPYT
```

OX40L is the ligand for CD134 and is expressed on such cells as DC2s (a subtype of dendritic cells) enabling amplification of Th2 cell differentiation. OX40L has also been designated CD252 (cluster of differentiation 252).

```
OX40L sequence
                                     (SEQ ID No. 22)
MERVQPLEENVGNAARPRFERNKLLLVASVIQGLGLLLCFTYICLHFSAL

QVSHRYPRIQSIKVQFTEYKKEKGFILTSQKEDEIMKVQNYLISLKGYFS

QEVNISLHYQKDEEPLFQLKKVRSVNSLMVASLTYKDKVYLNVTTDNTSL

DDFHVNGGELILIHQNPGEFCVL
```

41BBL is a cytokine that belongs to the tumour necrosis factor (TNF) ligand family. This transmembrane cytokine is a bidirectional signal transducer that acts as a ligand for 4-1BB, which is a costimulatory receptor molecule in T lymphocytes. 41BBL has been shown to reactivate anergic T lymphocytes in addition to promoting T lymphocyte proliferation.

```
41BBL sequence
                                     (SEQ ID No. 23)
MEYASDASLDPEAPWPPAPRARACRVLPWALVAGLLLLLLLAAACAVFLA

CPWAVSGARASPGSAASPRLREGPELSPDDPAGLLDLRQGMFAQLVAQNV

LLIDGPLSWYSDPGLAGVSLTGGLSYKEDTKELVVAKAGVYYVFFQLELR

RVVAGEGSGSVSLALHLQPLRSAAGAAALALTVDLPPASSEARNSAFGFQ

GRLLHLSAGQRLGVHLHTEARARHAWQLTQGATVLGLFRVTPEIPAGLPS

PRSE
```

Spacer Domain

The mitogenic T-cell activating transmembrane protein and/or cytokine-based T-cell activating transmembrane protein may comprise a spacer sequence to connect the antigen-binding domain with the transmembrane domain. A flexible spacer allows the antigen-binding domain to orient in different directions to facilitate binding.

The spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Examples of amino acid sequences for these spacers are given below:

```
(hinge-CH2CH3 of human IgG1)
                                     SEQ ID No. 24
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD

SEQ ID No. 25 (human CD8 stalk):
TTTPAPRPPTPAPTIASQPLSLRPEACRPAAGGAVHTRGLDFACDI

SEQ ID No. 26 (human IgG1 hinge):
AEPKSPDKTHTCPPCPKDPK (CD2 ectodomain)
                                     SEQ ID No. 27
KEITNALETWGALGQDINLDIPSFQMSDDIDDIKWEKTSDKKKIAQFRKE

KETFKEKDTYKLFKNGTLKIKHLKTDDQDIYKVSIYDTKGKNVLEKIFDL

KIQERVSKPKISWTCINTTLTCEVMNGTDPELNLYQDGKHLKLSQRVITH

KWTTSLSAKFKCTAGNKVSKESSVEPVSCPEKGLD (CD34 ectodomain)
                                     SEQ ID no. 28
SLDNNGTATPELPTQGTFSNVSTNVSYQETTTPSTLGSTSLHPVSQHGNE

ATTNITETTVKFTSTSVITSVYGNTNSSVQSQTSVISTVFTTPANVSTPE

TTLKPSLSPGNVSDLSTTSTSLATSPTKPYTSSSPILSDIKAEIKCSGIR

EVKLTQGICLEQNKTSSCAEFKKDRGEGLARVLCGEEQADADAGAQVCSL

LLAQSEVRPQCLLLVLANRTEISSKLQLMKKHQSDLKKLGILDFTEQDVA

SHQSYSQKT
```

The spacer sequence may be derived from a human protein. The spacer sequence may not be derived from a viral protein. In particular, the spacer sequence may not be, be derived from, or comprise part of the surface envelope subunit (SU) of a retroviral env protein.

Transmembrane Domain

The transmembrane domain is the sequence of the mitogenic T-cell activating transmembrane protein and/or cytokine-based T-cell activating transmembrane protein that spans the membrane. The transmembrane domain may comprise a hydrophobic alpha helix. The transmembrane domain may be derived from CD28, which gives good receptor stability.

The transmembrane domain may be derived from a human protein. The transmembrane domain may not be derived from a viral protein. In particular, the transmembrane domain may not be, be derived from, or comprise part of the transmembrane envelope subunit (TM) of a retroviral env protein.

An alternative option to a transmembrane domain is a membrane-targeting domain such as a GPI anchor.

GPI anchoring is a post-translational modification which occurs in the endoplasmic reticulum. Preassembled GPI anchor precursors are transferred to proteins bearing a C-terminal GPI signal sequence. During processing, the GPI anchor replaces the GPI signal sequence and is linked to the target protein via an amide bond. The GPI anchor targets the mature protein to the membrane.

The present tagging protein may comprise a GPI signal sequence.

Cytokine-Based T-Cell Activating Transmembrane Protein

The viral vector of the present invention may comprise a cytokine-based T-cell activating transmembrane protein in the viral envelope. The cytokine-based T-cell activating transmembrane protein is derived from the host cell during viral vector production. The cytokine-based T-cell activating transmembrane protein is made by the host cell and expressed at the cell surface. When the nascent viral vector buds from the host cell membrane, the cytokine-based T-cell activating transmembrane protein is incorporated in the viral envelope as part of the packaging cell-derived lipid bilayer.

The cytokine-based T-cell activating transmembrane protein is not produced from one of the viral genes, such as gag, which encodes the main structural proteins, or env, which encodes the envelope protein.

The cytokine-based T-cell activating transmembrane protein may comprise a cytokine domain and a transmembrane domain. It may have the structure C-S-TM, where C is the cytokine domain, S is an optional spacer domain and TM is the transmembrane domain. The spacer domain and transmembrane domains are as defined above.

Cytokine Domain

The cytokine domain may comprise part or all of a T-cell activating cytokine, such as from IL2, IL7 and IL15. The cytokine domain may comprise part of the cytokine, as long as it retains the capacity to bind its particular receptor and activate T-cells.

IL2 is one of the factors secreted by T cells to regulate the growth and differentiation of T cells and certain B cells. IL2 is a lymphokine that induces the proliferation of responsive T cells. It is secreted as a single glycosylated polypeptide, and cleavage of a signal sequence is required for its activity. Solution NMR suggests that the structure of IL2 comprises a bundle of 4 helices (termed A-D), flanked by 2 shorter helices and several poorly defined loops. Residues in helix A, and in the loop region between helices A and B, are important for receptor binding. The sequence of IL2 is shown as SEQ ID No. 29.

```
                                       SEQ ID No. 29
MYRMQLLSCIALSLALVTNSAPTSSSTKKTQLQLEHLLLDLQMILNGINNY
KNPKLTRMLTFKFYMPKKATELKHLQCLEEELKPLEEVLNLAQSKNFHLRP
RDLISNINVIVLELKGSETTFMCEYADETATIVEFLNRWITFCQSIISTLT
```

IL7 is a cytokine that serves as a growth factor for early lymphoid cells of both B- and T-cell lineages. The sequence of IL7 is shown as SEQ ID No. 30.

```
                                       SEQ ID No. 30
MFHVSFRYIFGLPPLILVLLPVASSDCDIEGKDGKQYESVLMVSIDQLL

DSMKEIGSNCLNNEFNFFKRHICDANKEGMFLFRAARKLRQFLKMNSTG

DFDLHLLKVSEGTTILLNCTGQVKGRKPAALGEAQPTKSLEENKSLKEQ

KKLNDLCFLKRLLQEIKTCWNKILMGTKEH
```

IL15 is a cytokine with structural similarity to IL-2. Like IL-2, IL-15 binds to and signals through a complex composed of IL-2/IL-15 receptor beta chain and the common gamma chain. IL-15 is secreted by mononuclear phagocytes, and some other cells, following infection by virus(es). This cytokine induces cell proliferation of natural killer cells; cells of the innate immune system whose principal role is to kill virally infected cells. The sequence of IL-15 is shown as SEQ ID No. 31.

```
                                       SEQ ID No. 31
MRISKPHLRSISIQCYLCLLLNSHFLTEAGIHVFILGCFSAGLPKTEANWV

NVISDLKKIEDLIQSMHIDATLYTESDVHPSCKVTAMKCFLLELQVISLES

GDASIHDTVENLIILANNSLSSNGNVTESGCKECEELEEKNIKEFLQSFVH

IVQMINTS
```

The cytokine-based T-cell activating transmembrane protein may comprise one of the following sequences, or a variant thereof:

```
(membrane-IL7)
                                       SEQ ID No. 32
MAHVSFRYIFGLPPLILVLLPVASSDCDIEGKDGKQYESVLMVSIDQLLD

SMKEIGSNCLNNEFNFFKRHICDANKEGMFLFRAARKLRQFLKMNSTGDF

DLHLLKVSEGTTILLNCTGQVKGRKPAALGEAQPTKSLEENKSLKEQKKL

NDLCFLKRLLQEIKTCWNKILMGTKEHSGGGSPAKPTTTPAPRPPTPAPT

IASQPLSLRPEACRPAAGGAVHTRGLDFACDIYIWAPLAGTCGVLLLSLV

ITLYCNHRNRRRVCKCPRPVV (membrane-IL15)
                                       SEQ ID No. 33
MGLVRRGARAGPRMPRGWTALCLLSLLPSGFMAGIHVFILGCFSAGLPKT

EANWVNVISDLKKIEDLIQSMHIDATLYTESDVHPSCKVTAMKCFLLELQ

VISLESGDASIHDTVENLIILANNSLSSNGNVTESGCKECEELEEKNIKE

FLQSFVHIVQMFINTSSPAKPTTTPAPRPPTPAPTIASQPLSLRPEACRP

AAGGAVHTRGLDFACDIYIWAPLAGTCGVLLLSLVITLYCNHRNRRRVCK

CPRPVV
```

The cytokine-based T-cell activating transmembrane protein may comprise a variant of the sequence shown as SEQ ID No. 32 or 33 having at least 80, 85, 90, 95, 98 or 99% sequence identity, provided that the variant sequence is a cytokine-based T-cell activating transmembrane protein having the required properties i.e. the capacity to activate a T cell when present in the envelope protein of a retroviral or lentiviral vector.

Tagging Protein

The viral envelope of the viral vector may also comprise a tagging protein which comprises a binding domain which binds to a capture moiety and a transmembrane domain.

The tagging protein may comprise:

a binding domain which binds to a capture moiety a spacer; and a transmembrane domain.

The tagging protein facilitates purification of the viral vector from cellular supernatant via binding of the tagging protein to the capture moiety.

'Binding domain' refers to an entity, for example an epitope, which is capable recognising and specifically binding to a target entity, for example a capture moiety.

The binding domain may comprise one or more epitopes which are capable of specifically binding to a capture moiety. For example the binding domains may comprise at least one, two, three, four or five epitopes capable of specifically binding to a capture moiety. Where the binding domain comprises more than one epitope, each epitope may be separated by a linker sequence, as described herein.

The binding domain may be releasable from the capture moiety upon the addition of an entity which has a higher binding affinity for the capture moiety compared to the binding domain.

Streptavidin-Binding Epitope

The binding domain may comprise one or more streptavidin-binding epitope(s). For example, the binding domain may comprise at least one, two, three, four or five streptavidin-binding epitopes.

Streptavidin is a 52.8 kDa protein purified from the bacterium *Streptomyces avidinii*. Streptavidin homo-tetramers have a very high affinity for biotin (vitamin B7 or vitamin H), with a dissociation constant (Kd)~$10^{-15}$ M. Streptavidin is well known in the art and is used extensively in molecular biology and bionanotechnology due to the streptavidin-biotin complex's resistance to organic solvents, denaturants, proteolytic enzymes, and extremes of temperature and pH. The strong streptavidin-biotin bond can be used to attach various biomolecules to one another or on to a solid support. Harsh conditions are needed to break the streptavidin-biotin interaction, however, which may denature a protein of interest being purified.

The binding domain may be, for example, a biotin mimic. A 'biotin mimic' may refer to an short peptide sequence (for example 6 to 20, 6 to 18, 8 to 18 or 8 to 15 amino acids) which specifically binds to streptavidin.

As described above, the affinity of the biotin/streptavidin interaction is very high. It is therefore an advantage of the present invention that the binding domain may comprise a biotin mimic which has a lower affinity for streptavidin compared to biotin itself.

In particular, the biotin mimic may bind streptavidin with a lower binding affinity than biotin, so that biotin may be used to elute streptavidin-captured retroviral vectors. For example, the biotin mimic may bind streptavidin with a Kd of 1 nM to 100 uM.

The biotin mimic may comprise a sequence as shown in Table 1.

TABLE 1

Biotin mimicking peptides.

| name | Sequence | affinity |
|---|---|---|
| Long nanotag | EVEAVEDERVPINET (gEdifini5: E6) | 3.6 nM |
| Short nanotag | DVEAWLGAR (SEQ ID NO: 40) | 17 nM |
| Streptag | WRHPQFGG (SEQ ID NO: 41) | |
| streptagII | WSHPQFEK (SEQ ID NO: 36) | 72 uM |
| SBP-tag | MDEKTTGWRGGHVVEGLAGELEQLRARLEHHPQGQREP SEQ ID NO: 42) | 2.5 nM |
| ccstreptag | CHPQGPPC (SEQ ID NO: 38) | 230 nM |
| flankedccstreptag | AECHPQGPPCIEGRK (SEQ ID NO: 37) | |

The biotin mimic may be selected from the following group: StreptagII, Flankedccstreptag and ccstreptag.

The binding domain may comprise more than one biotin mimic. For example the binding domain may comprise at least one, two, three, four or five biotin mimics.

Where the binding domain comprises more than one biotin mimic, each mimic may be the same or a different mimic. For example, the binding domain may comprise two StreptagII biotin mimics separated by a linker (for example as shown by SEQ ID NO: 43) or two Flankedccstreptag separated by a linker (for example as shown by SEQ ID NO: 44).

(StreptagII-d8-x2)
SEQ ID NO: 43
WSHPQFEKSGGGGSPAPRPPTPAPTIASWSHPQFEK (Flankedccstreptag-d8-x2)
SEQ ID NO: 44
ECHPQGPPCIEGRKSSGGGGSPAPRPPTPAPTIASECHPQGPPCIEGR
KS Glutathione S-Transferase The binding domain may comprise a glutathione S-transferase (GST) domain.

GSTs comprise a family of eukaryotic and prokaryotic phase II metabolic isozymes which catalyze the conjugation of the reduced form of glutathione (GSH) to xenobiotic substrates for the purpose of detoxification. The GST family consists of three superfamilies: the cytosolic, mitochondrial, and microsomal (also known as MAPEG) proteins (Udomsinpraser et al. Biochem. J. (2005) 388 (Pt 3): 763-71).

The GST protein has a strong binding affinity for GSH and this interaction is commonly used in molecular biology to enable the isolation of a GST-tagged protein from a protein mixture.

An amino acid sequence for GST is shown as SEQ ID NO: 45.

(GST)
SEQ ID NO: 45
MGTSLLCWMALCLLGADHADAMSPILGYWKIKGLVQPTRLLLEYLEEKYE

EHLYERDEGDKWRNKKFELGLEFPNLPYYIDGDVKLTQSMAIIRYIADKH

NMLGGCPKERAEISMLEGAVLDIRYGVSRIAYSKDFETLKVDFLSKLPEM

LKMFEDRLCHKTYLNGDHVTHPDFMLYDALDVVLYMDPMCLDAFPKLVCF

-continued
KKRIEAIPQIDKYLKSSKYIAWPLQGWQATFGGGDHPPKSDLEVLFQGPL

G

Rituximab-Binding Epitope

The present tagging protein may comprise a binding domain which comprises a rituximab-binding epitope (R epitope) and/or a Qbend10 epitope (Q epitope).

A rituximab-binding epitope refers to an epitope which specifically binds rituximab. For example, the rituximab-binding epitope may be based on the CD20 B-cell antigen.

The Rituximab-binding epitope sequence from CD20 is CEPANPSEKNSPSTQYC (SEQ ID No.46)

Perosa et al (2007, J. Immunol 179:7967-7974) describe a series of cysteine-constrained 7-mer cyclic peptides, which bear the antigenic motif recognised by the anti-CD20 mAb Rituximab but have different motif-surrounding amino acids. Eleven peptides were described in all, as shown in the following table:

| Peptide | Insert sequence |
|---|---|
| R15-C | acPYANPSLc (SEQ ID No. 47) |
| R3-C | acPYSNPSLc (SEQ ID No. 48) |
| R7-C | acPFANPSTc (SEQ ID No. 49) |
| R8-, R12-, R18-C | acNFSNPSLc (SEQ ID No. 50) |
| R14-C | acPFSNPSMc (SEQ ID No. 51) |
| R16-C | acSWANPSQc (SEQ ID No. 52) |
| R17-C | acMFSNPSLc (SEQ ID No. 53) |
| R19-C | acPFANPSMc (SEQ ID No. 54) |
| R2-C | acWASNPSLc (SEQ ID No. 55) |
| R10-C | acEHSNPSLc (SEQ ID No. 56) |
| R13-C | acWAANPSMc (SEQ ID No. 57) |

Li et al (2006 Cell Immunol 239:136-43) also describe mimetopes of Rituximab, including the sequence:

QDKLTQWPKWLE. (SEQ ID No. 58)

The polypeptide of the present invention comprises a Rituximab-binding epitope having an amino acid sequence selected from the group consisting of SEQ ID No. 46-58 or a variant thereof which retains Rituximab-binding activity.

OBend10

The CliniMACS CD34 selection system utilises the QBEnd10 monoclonal antibody to achieve cellular selection. The present inventors have previously mapped the QBEnd10-binding epitope from within the CD34 antigen (see WO 2013/153391) and determined it to have the amino acid sequence shown as SEQ ID No. 59.

ELPTQGTFSNVSTNVS. (SEQ ID No. 59)

The binding domain of the present tagging protein the present invention may comprise a QBEnd10-binding epitope having the amino acid sequence shown as SEQ ID No. 59 or a variant thereof which retains QBEnd10-binding activity.

RQR8

The tagging protein may comprise a binding domain which comprises or consists of 136 amino acid sequence shown as SEQ ID NO: 60.

(RQR8)
SEQ ID NO: 60
CPYSNPSLCSGGGGSELPTQGTFSNVSTNVSPAKPTTTACPYSNPSLCSG
GGGSPAPRPPTPAPTIASQPLSLRPEACRPAAGGAVHTRGLDFACDIYIW
APLAGTCGVLLLSLVITLYCNHRNRRRVCKCPRPVV

Nucleic Acid

The invention also relates to a nucleic acid encoding a cytokine-based T-cell activating transmembrane protein or a nucleic acid encoding a mitogenic T-cell activating transmembrane protein. The nucleic acid may be in the form of a construct comprising a plurality of sequences encoding a mitogenic T-cell activating transmembrane protein and/or a cytokine-based T-cell activating transmembrane protein.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

The nucleic acid may produce a polypeptide which comprises one or more sequences encoding a mitogenic T-cell activating transmembrane protein and/or one or more sequences encoding a cytokine-based T-cell activating transmembrane protein. The cleavage site may be self-cleaving, such that when the polypeptide is produced, it is immediately cleaved into the receptor component and the signalling component without the need for any external cleavage activity.

Various self-cleaving sites are known, including the Foot-and-Mouth disease virus (FMDV) 2a self-cleaving peptide and various variants and 2A-like peptides. The peptide may have the sequence shown as SEQ ID No. 34 or 35.

RAEGRGSLLTCGDVEENPGP. SEQ ID No. 34

QCTNYALLKLAGDVESNPGP SEQ ID No 35

The co-expressing sequence may be an internal ribosome entry sequence (IRES). The co-expressing sequence may be an internal promoter.

Vector

The present invention also provides a vector, or kit of vectors which comprises one or more sequences encoding a mitogenic T-cell activating transmembrane protein and/or one or more sequences encoding a cytokine-based T-cell activating transmembrane protein. Such a vector may be used to introduce the nucleic acid sequence(s) into a host cell, such as a producer or packaging cell.

The vector may, for example, be a plasmid or a viral vector, such as a retroviral vector or a lentiviral vector, or a transposon based vector or synthetic mRNA.

The vector may be capable of transfecting or transducing a host cell.

Method

The invention also provides a method for making an activated transgenic T-cell or natural killer (NK) cell, which comprises the step of transducing a T or NK cell with a retroviral or lentiviral vector according to the invention, such that the T-cell or NK cell is activated by one or more mitogenic T-cell activating transmembrane protein(s) and optionally one or more cytokine-based T-cell activating transmembrane protein(s).

The method for transducing and activating T cells or NK calls may take 48 hours or less, for example between 24 and 48 hours.

The invention will now be further described by way of Examples, which are meant to serve to assist one of ordinary skill in the art in carrying out the invention and are not intended in any way to limit the scope of the invention.

EXAMPLES

Example 1—Production of Viral Vectors Displaying OKT3 on the Virion Surface

An initial proof-of-concept experiment was performed where it was demonstrated that expression of an OKT3 scFv on the packaging cell results the production of viral vector which causes the mitogenic activation of T-cell targets.

Figure 2:
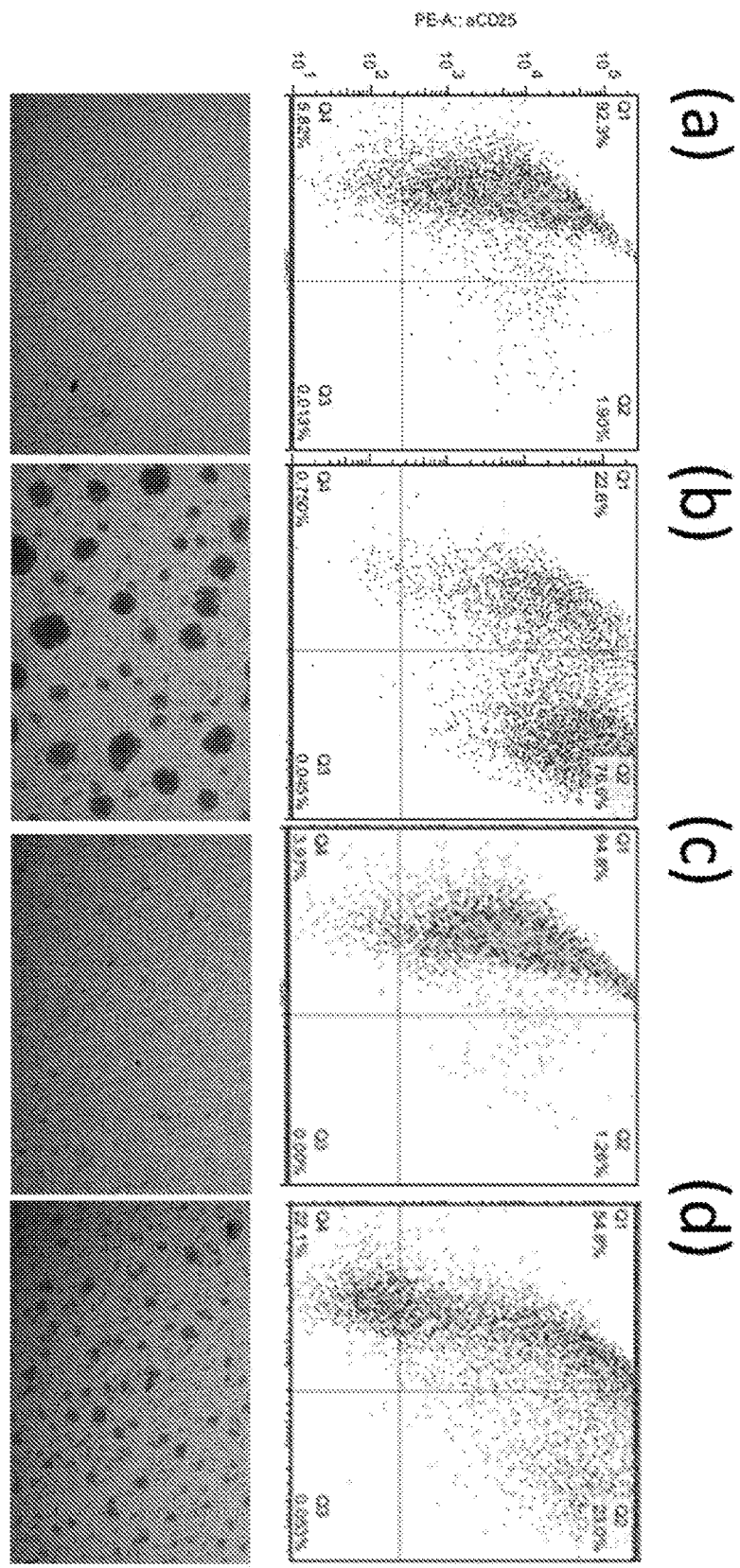
FIG. 2—Demonstration that an OKT3 scFv can be incorporated into a lentivirus. Results show activation of T cells (a) non-stimulated—transduced with lentiviral vector from 293T cells; (b) stimulated with OKT3, CD28.2 and IL2—transduced with lentiviral vector from 293T cells; (c) non-stimulated—transduced with supernatant from 293T.OKT3, transfected with only the transfer vector; (d) non-stimulated—transduced with lentiviral vector from 293T.OKT3. Top panel shows scatter-plots of transduction (x-axis), and activation by CD25 expression (y-axis). Bottom panel show photomicrographs of T-cell cultures. Clumping indicated activation.

OKT3 scFv 293T cells produced a lentiviral vector which caused activation and transduction of target T-cells. This mitogenic property was dependent on the presence of lentiviral helper components i.e. the effect was not due to a non-specific property of the packaging cell supernatant (FIG. 2).

A comparison of the OKT3 scFv attached to the membrane via a CD8 stalk or via an IgG1 hinge's ability to incorporate into the lentivirus and cause a mitogenic stimulus was also made, with no difference noted between the two spacers.

Figure 3:
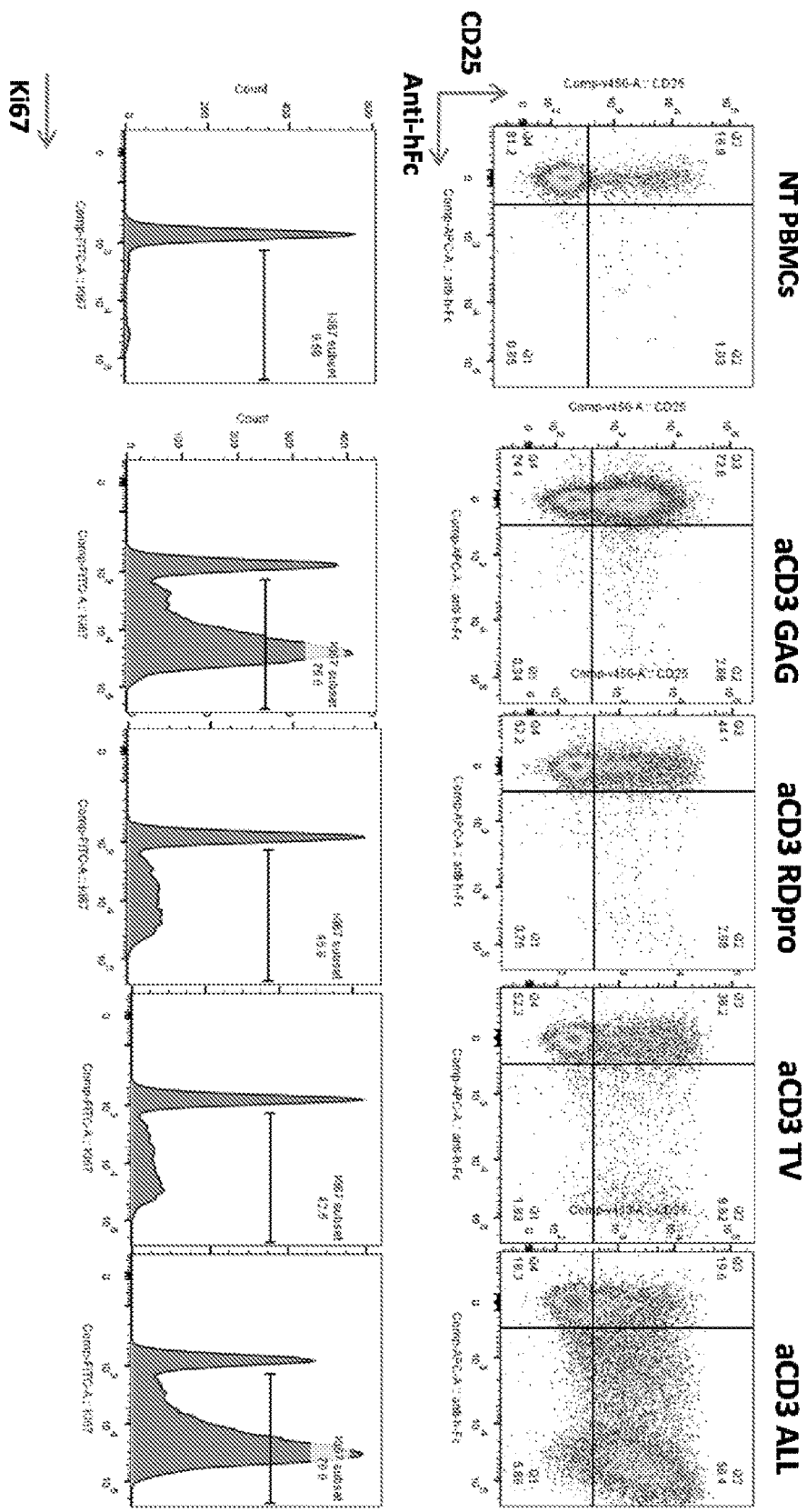
FIG. 3—Demonstration that mitogenic stimulation and transduction of T cells is dependent on gagpol. 293T cells stably expressing surface bound OKT3 were transfected with gagpol, RD-PRO env, the transfer vector or all three plasmids along with rev. The subsequent supernatant was applied to primary human T-cells. The T-cells were studied by flow-cytometry with the following parameters: CD25 to measure T-cell activation; anti-Fc to detect transgene which was a CAR with an Fc spacer; ki67 to determine cells in cycle. Only conditions where gagpol was supplied resulted in significant mitogenic stimulation. Only the condition where all plasmids were supplied (along with rev) resulted in mitogenic stimulation of T-cells and transduction.

293T cells stably expressing surface bound OKT3 were transfected with lentiviral gagpol, RD-PRO env, the transfer vector or all three plasmids along with a lentiviral rev expressing plasmid. The subsequent supernatant was applied to primary human T-cells. The T-cells were subsequently studied by flow-cytometry with the following parameters: CD25 to measure T-cell activation; anti-Fc to detect transgene (CAR with an Fc space)r; ki67 to determine cells in cycle (FIG. 3). Only conditions where gagpol was supplied resulted in significant mitogenic stimulation.

Figure 4:
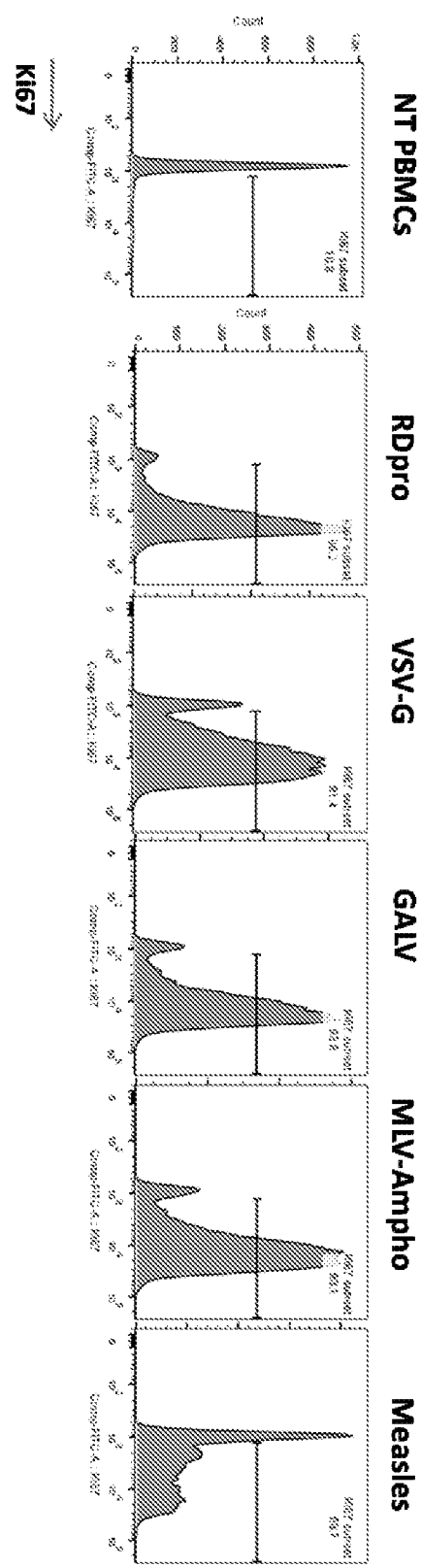
FIG. 4—Demonstration that different lentiviral pseudotyping supports the mitogenic effect. 293T cells stably expressing the membrane bound OKT3 were transfected with a lentiviral transfer vector, lentiviral gagpol, rev and different env plasmids: namely VSV-G, RD-PRO, Ampho, GALV and Measles M/H. The subsequent supernatant was applied to primary human T-cells. The cells were subsequently stained with ki67 and studied by flow-cytometry. All pseudotypes supported the mitogenic effect, although the effect seemed reduced with Measles pseudotyping.

Only the condition where all plasmids were supplied (along with rev) resulted in mitogenic stimulation of T-cells and transduction Further experiments were also conducted to determine if different lentiviral pseudotyping supports the mitogenic effect. 293T cells stably expressing the membrane bound OKT3 were transfected with a lentiviral transfer vector, lentiviral gagpol, rev and different env plasmids: namely VSV-G, RD-PRO, Ampho, GALV and Measles M/H. The subsequent supernatant was applied to primary human T-cells. The cells were subsequently stained with ki67 and studied by flow-cytometry. All pseudotypes supported the mitogenic effect, although the effect seemed reduced with Measles pseudotyping (FIG. 4).

Example 2—Two Separate Mitogenic Stimuli can be Incorporated into the Viral Vector An additional construct which comprised the anti-CD28 activating scFv from antibody 15E8 was generated. The OKT3 scFv cassette (described above) expressed eGFP and the 15E8 scFv cassette expressed the blue fluorescent protein eBFP2.

293T cells were generated which co-expressed high levels of eGFP and eBFP2, demonstrating the successful expression of both OKT3 and 15E8 on the surface of the 293T cells.

Figure 6:
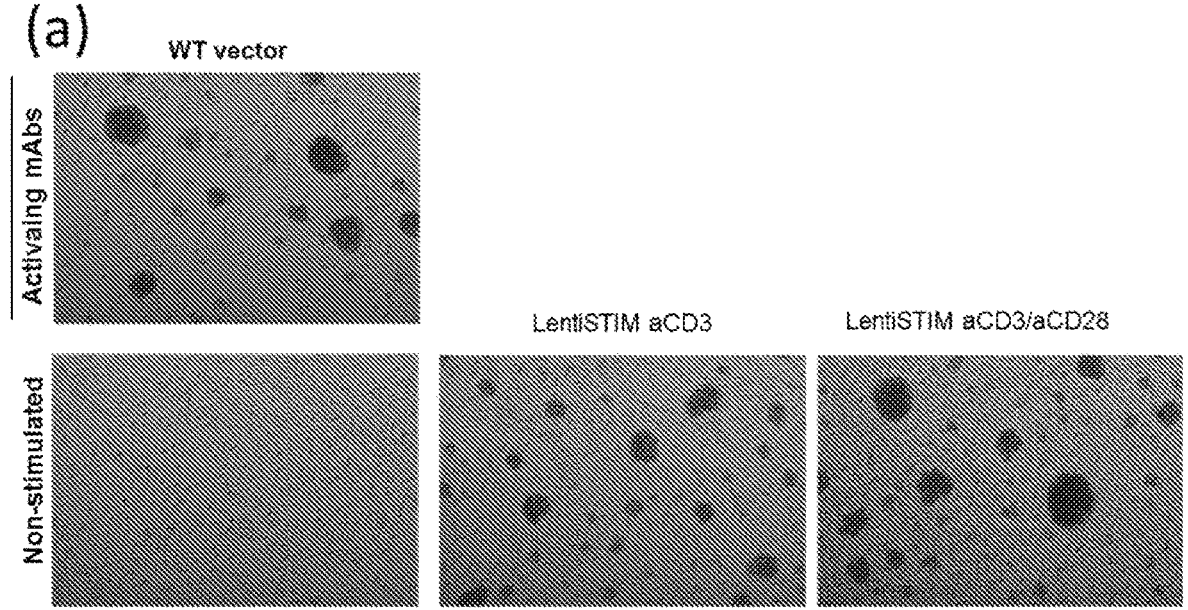
FIG. 6—Demonstration that two different mitogenic stimuli can be incorporated into the viral vector and that an anti-CD3/TCR stimulus along with an anti-CD28 stimulus has an improved effect compared to anti-CD3/TCR alone.
Figure 6:
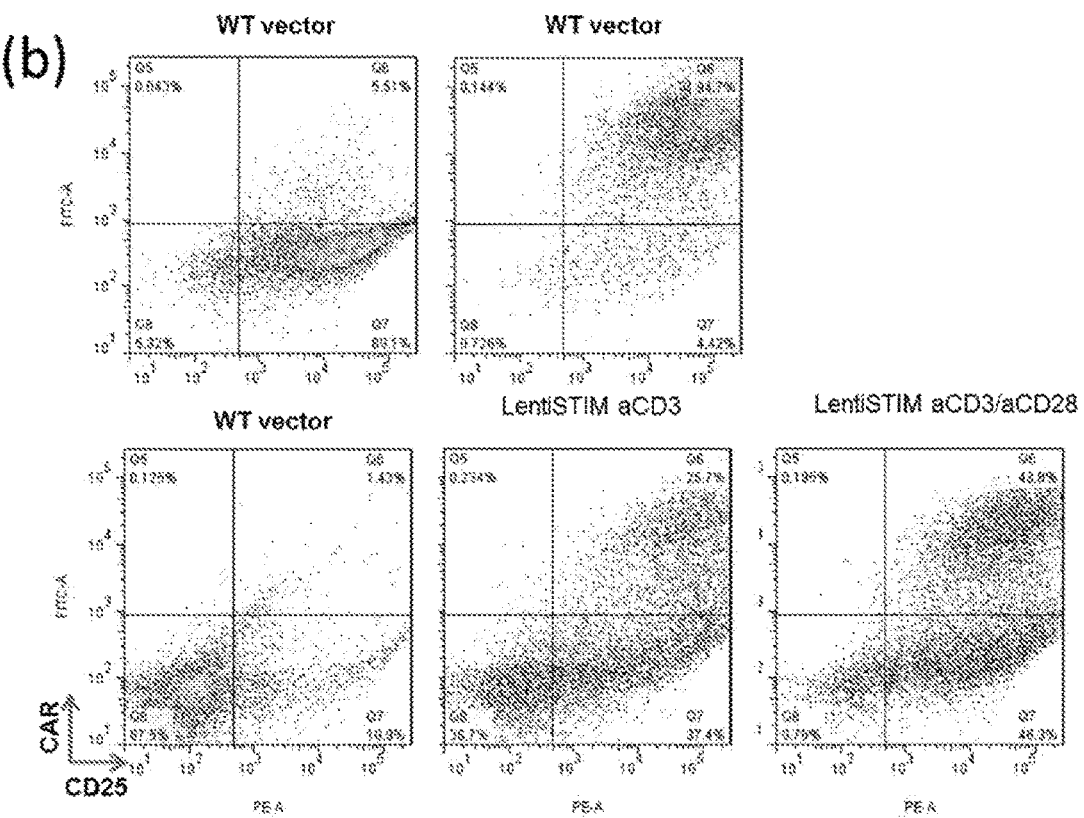
Figure 7:
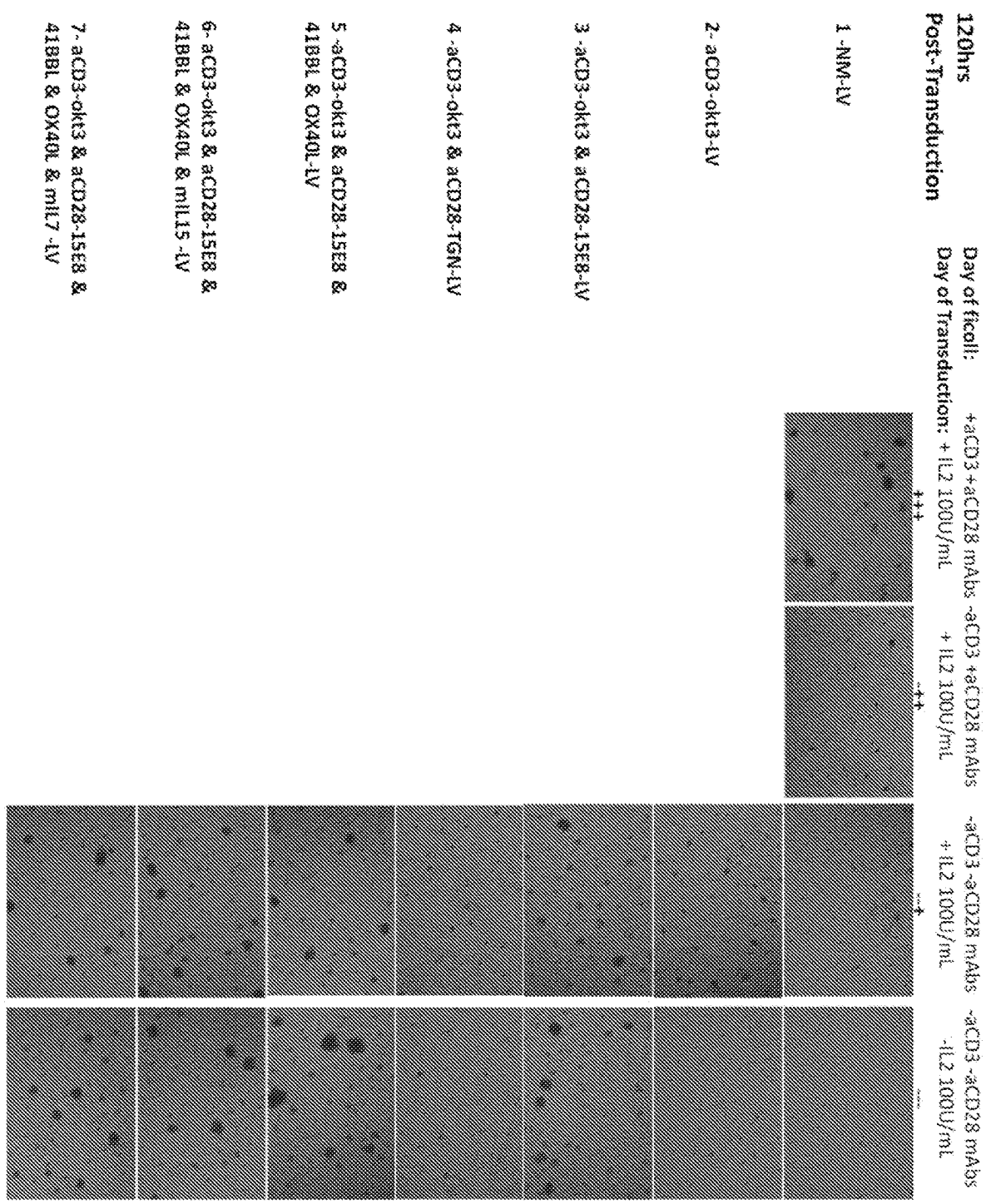
FIG. 7—Low resolution microscopy of T-cells stimulated with different lentiviral vectors generated from 293T cells expressing different elements on their cell surface.
Figure 8:
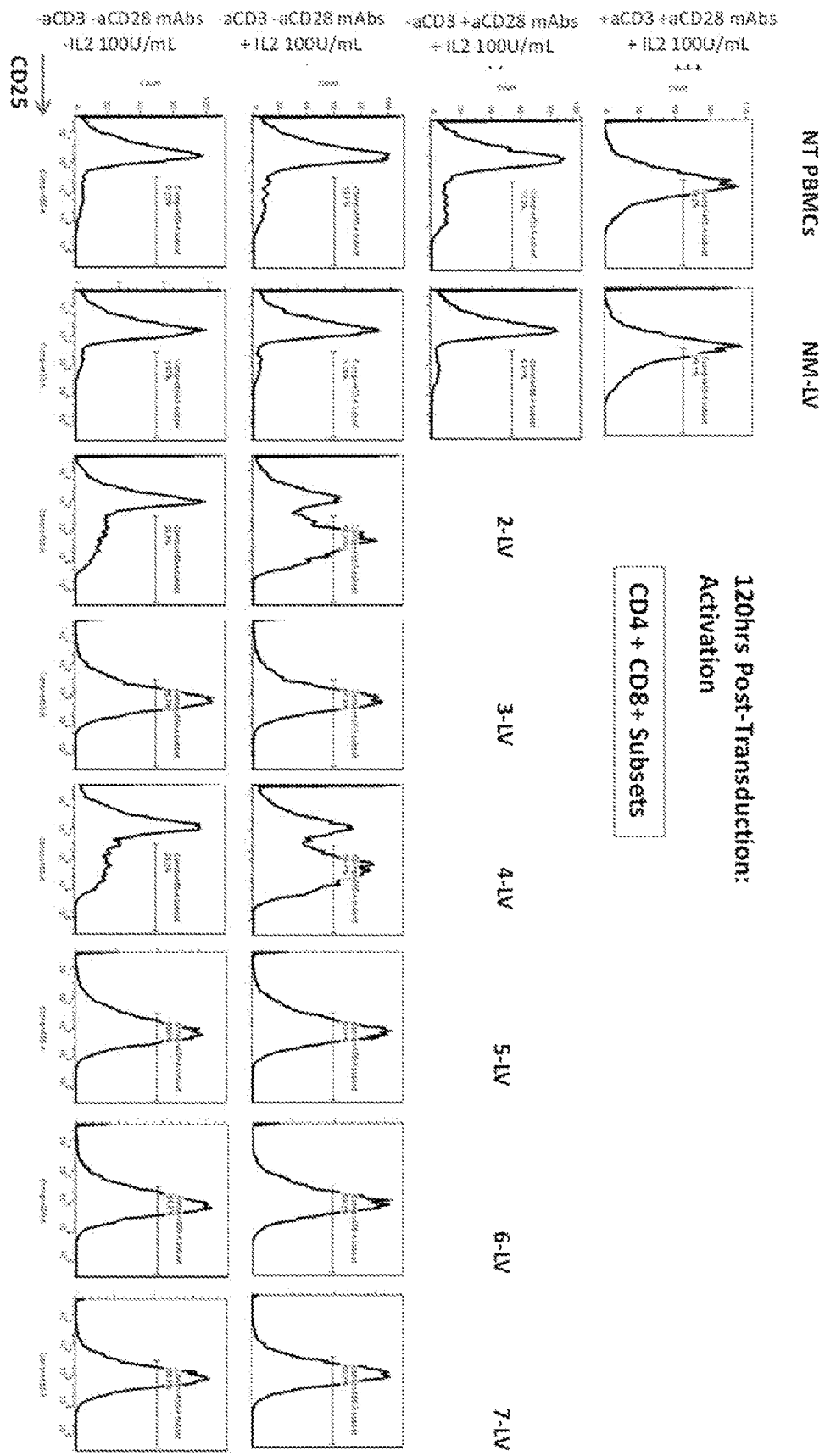
FIG. 8—Activation of CD4 and CD8 T cells following transduction with lentiSTIM vectors displaying different combinations of mitogenic and cytokine peptides. Activation is determined by CD25 expression at 120-hours post-transduction.
Figure 9:
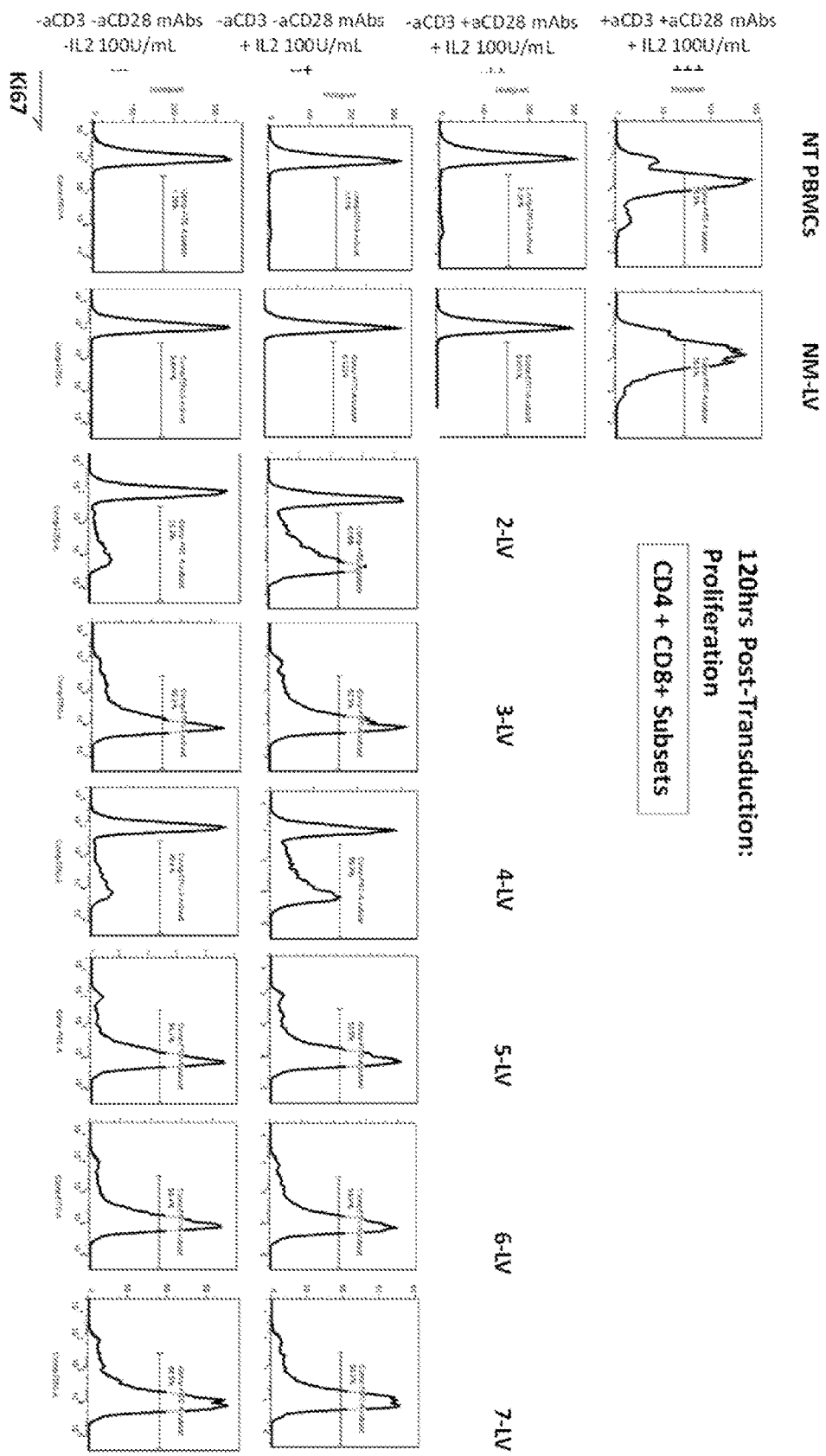
FIG. 9—Proliferation of CD4 and CD8 T cells following transduction with lentiSTIM vectors displaying different combinations of mitogenic and cytokine peptides. Proliferation is determined by Ki67 expression at 120-hours post-transduction.
Figure 10:
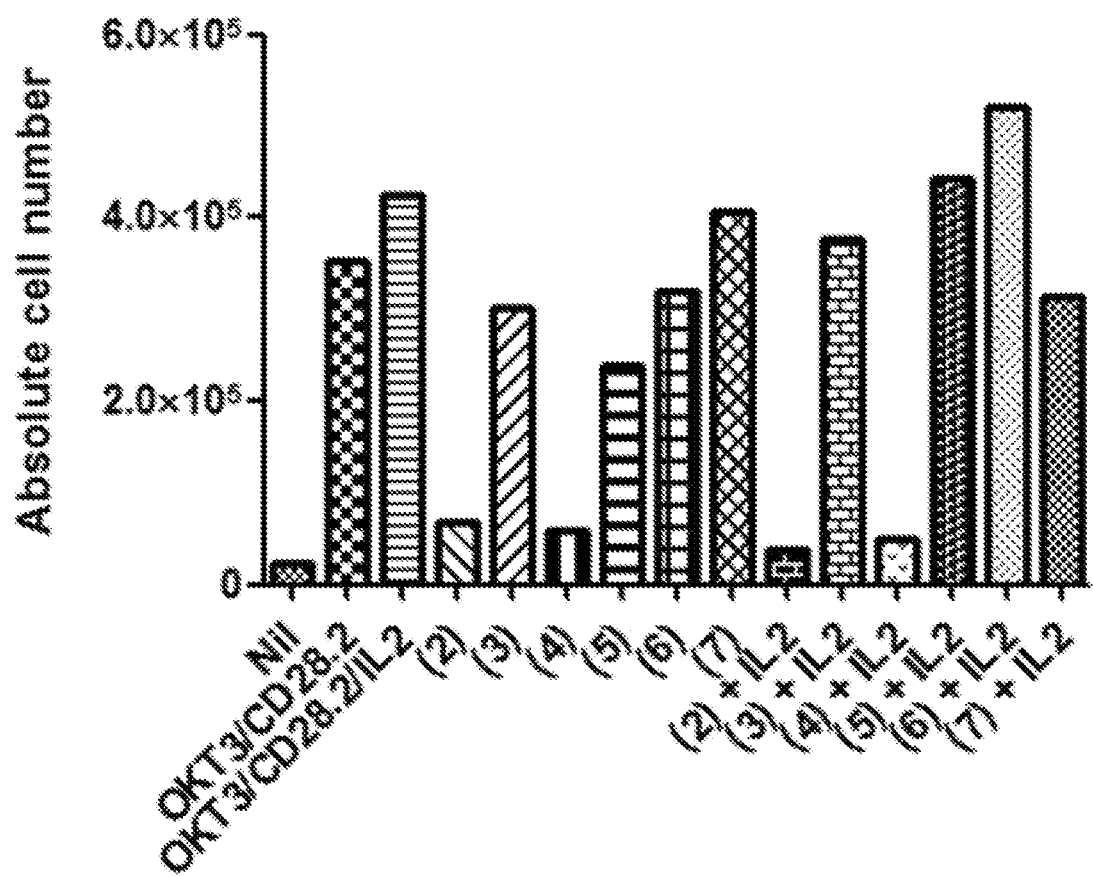
FIG. 10—Expansion of T cells following transduction with lentiSTIM vectors displaying different combinations of mitogenic and cytokine peptides. Expansion is determined by absolute cell counts at 120-hours post-transduction.

Lentiviral supernatant was generated from wild-type 293T cells, 293T cells which expressed OKT3 scFv alone and 293T cells which expressed both OKT3 and 15E8. Activation levels and transduction efficiency was greater with the two stimulations (FIG. 6).

Figure 5:
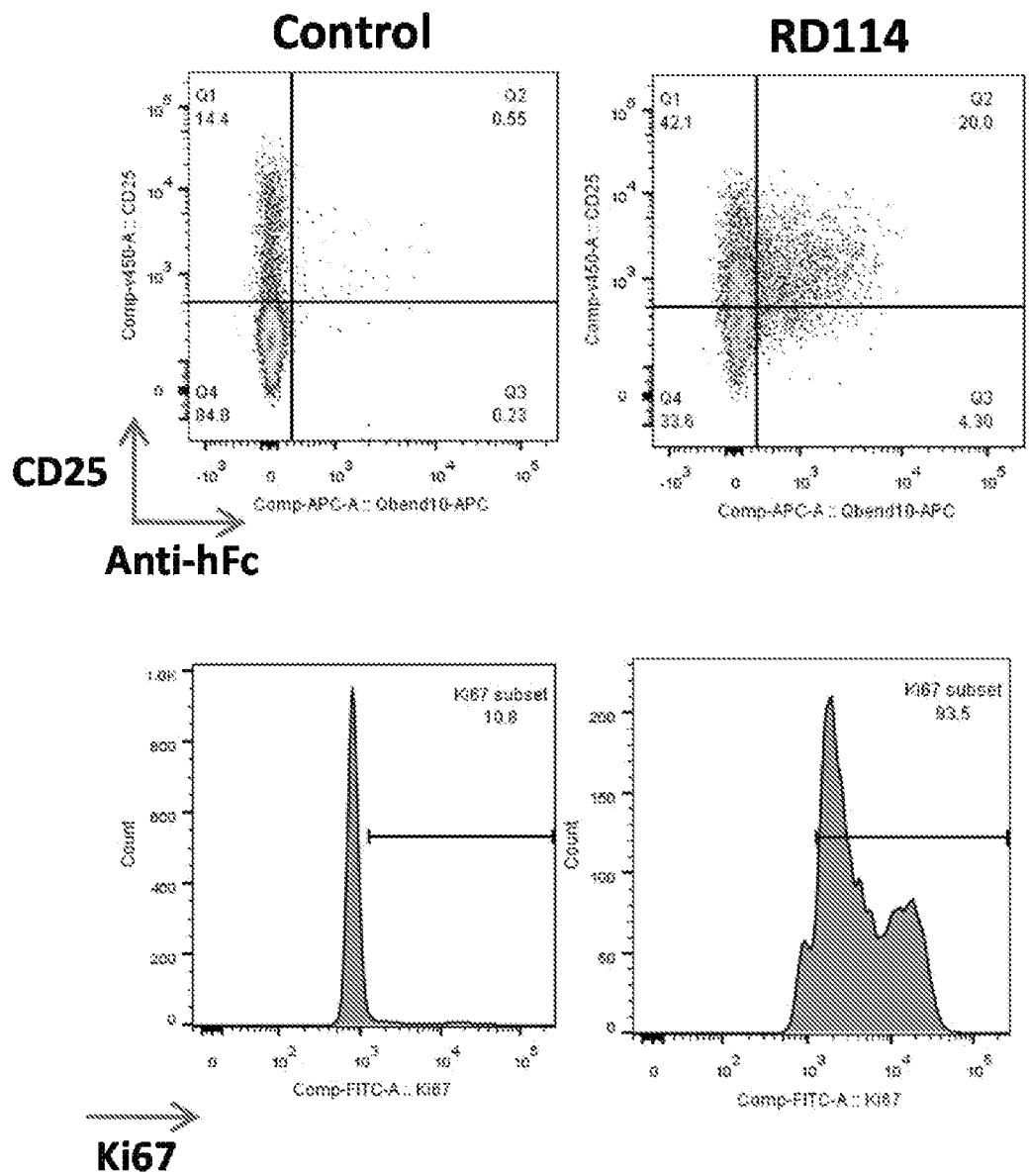
FIG. 5—Demonstration that mitogenic stimulation and transduction of T cells is achieved with a gamma-retroviral vector. 293T cells stably expressing membrane bound OKT3 were transfected with a gamma-retroviral transfer vector coding for a CAR, gamma-retroviral gagpol expression plasmid and an RD114 expression plasmid. Subsequent supernant was applied to primary human T-cells. The T-cells were subsequently stained with anti-Fc, anti-CD25 and ki67 and studied by flow-cytometry. Although no mitogenic stimulus was applied, T-cells were activated, cycling and were expressing transgene.

Example 3—Demonstration of Functionality in Gamma-Retroviral Vectors 293T cells stably expressing membrane bound OKT3 were transfected with a gamma-retroviral transfer vector coding for a CAR, gamma-retroviral gagpol expression plasmid and an RD114 expression plasmid. Subsequent supernant was applied to primary human T-cells. The T-cells were stained with anti-Fc, anti-CD25 and ki67 and studied by flow-cytometry. Although no mitogenic stimulus was applied, T-cells were activated, cycling and were expressing transgene (FIG. 5)

Example 4—Combinations of Peptides Incorporated into Lentivirus Vectors

Different combinations of elements were incorporated into packaging cell lines. This included TGN1412 scFv which is a super-agonistic anti-CD28 mAb. Cytokines IL7 and IL15, as well as OX40L and 41BBL were also incorporated in different combinations as follows:
1. (Nil)
2. OKT3
3. OKT3+15E8
4. OKT3+TGN1412
5. OKT3+15E8+OX40L+41BBL
6. OKT3+15E8+OX40L+41BBL+mIL15
7. OKT3+15E8+OX40L+41BBL+mIL7

Lentiviral vector generated from these different 293T cells was used to stimulate/transduce T-cells.

Vector generated from non-engineered 293T cells along with mitogenic soluble antibodies OKT3 and CD28.2+/−IL2 was used as a control. Activation (CD25), proliferative fraction (Ki67) and absolute counts at day 5 were measured (FIGS. 7-10).

It was once again noted that there was a marked advantage of incorporating two signals instead of one. It was also noted that activation using mitogenic peptides displayed on the virion surface was markedly superior to the activation achieved by adding soluble antibodies to the T-cells.

Similar levels of proliferation to that of mAb activation with cytokine were also achieved.

Methodology

The VH and VL of mitogenic antibodies were cloned as scFvs and connected to a spacer domain, a TM domain and a polar anchor (SEQ ID Nos 1-3 above)

Cytokines were connected in frame to a spacer, a TM domain and a polar anchor (SEQ ID Nos 32 and 33 above).

For native co-stimulatory molecules such as 41BBL and OX40L, these are cloned in their native forms.

Each of the above types of membrane-bound proteins could then be stably expressed at high-levels on a 293T cell.

Viral vectors were made from these 293T cells using standard transient transfection. For lentiviral vector the transfer vector, rev expression vector, a lenti gagpol expression vector and the RD-PRO expression vector were co-transfected. For gamma retroviral vectors, the 293T cells were co-transfected with the transfer vector, MoMLV gagpol and RD114 expression plasmid. The supernatant was clarified by centrifugation and filtration with a 0.45 uM filter. The virus was applied to primary human T-cells on a retronectin plate. IL2 is added in some conditions, or no cytokines are added in other conditions.

Example 5—Comparing T Cell Subset Phenotypes from Cells Stimulated with Lentiviral Vector Versus Cells Stimulated with antiCD3/antiCD28 Antibody-Coated Beads Mononuclear cells were isolated from peripheral blood using standard techniques. Peripheral blood mononuclear cells (PBMCs) were then treated with either:
(i) antiCD3/antiCD28 antibody-coated beads (Dynabeads® Human T-Activator CD3/CD28) in a 3:1 ratio in the presence of non-modified lentiviral vector and IL15/IL7; or
(ii) lentiviral vector expressing OKT3 and 15E8B (combination 3 as described in Example 4) on a retronectin-coated plate in the presence of IL15 and IL7.

After 48 hours, cells were harvested and stained with a panel of T-cell phenotyping antibodies, as follows:
aCD4-BV650
aCD8-PE.Cy7
aCD45RO-BV605
aCD45RA-FITC
aCD95-PB
aCD197-BV685

Figure 11:
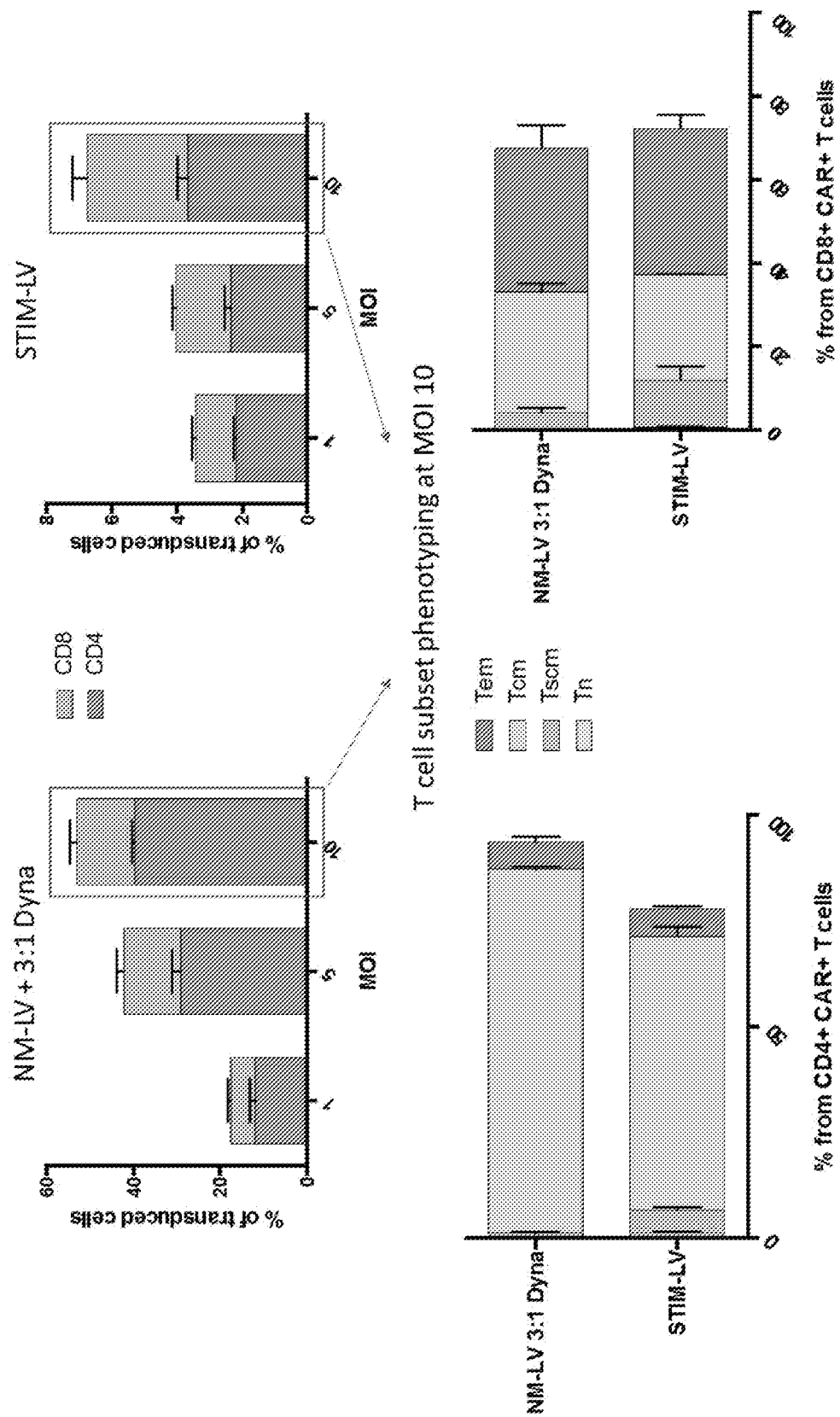
FIG. 11—Examining the T cell subset phenotype of PBMCs activated with either lentiSTIM vectors expressing anti-CD3 and anti-CD28 antibodies, or beads coated with anti-CD3 and anti-CD28 antibodies. NM-LV=non-modified lentivirus; STIM-LV=lentiSTIM vector; Tem=effector memory T cells; Tcm=central memory T cells; Tscm=stem memory T cells; and Tn=naïve T cells.

T cell subsets were analysed by FACS and the results are summarised in FIG. 11. For both the CD4+ and CD8+ T cell subsets, the cells stimulated with virus showed a greater proportion of naïve T cells (Tn and Tscm) than cells stimulated with antibody-coated beads.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A retroviral or lentiviral vector having a viral envelope which comprises:
   (i) a first mitogenic T-cell activating transmembrane protein which comprises a mitogenic domain which binds CD3, and a transmembrane domain; and
   (ii) a second mitogenic T cell activating transmembrane protein which comprises a mitogenic domain which binds CD28 and a transmembrane domain
   wherein the mitogenic T cell activating transmembrane proteins are not part of a viral envelope glycoprotein.

2. The viral vector according to claim 1, which comprises a cytokine-based T-cell activating transmembrane protein which comprises a cytokine selected from IL2, IL7 and IL15.

3. The viral vector according to claim 1, wherein the viral envelope also comprises:
   (iii) a tagging protein which comprises:
      a binding domain which binds to a capture moiety; and
      a transmembrane domain
   which tagging protein facilitates purification of the viral vector from cellular supernatant via binding of the tagging protein to the capture moiety.

4. The viral vector according to claim 1 which comprises a nucleic acid sequence encoding a T-cell receptor or a chimeric antigen receptor.

5. The viral vector according to claim 1 which is a virus-like particle (VLP).

6. A host cell which expresses, at the cell surface,
   (i) a first mitogenic T-cell activating transmembrane protein which comprises a mitogenic domain which binds CD3 and a transmembrane domain; and
   (ii) a second mitogenic T cell activating transmembrane protein which comprises a mitogenic domain which binds CD28 and a transmembrane domain;
   and which produces a retroviral or lentiviral vector according to claim 1.

7. The host cell according to claim 6, which also expresses, at the cell surface:
   (iii) a tagging protein which comprises:
      a binding domain which binds to a capture moiety; and
      a transmembrane domain;
   wherein the viral envelope of the retroviral or lentiviral vector produced by the host cell comprises the tagging protein,
   which tagging protein facilitates purification of the retroviral or lentiviral vector from the cellular supernatant via binding of the tagging protein to the capture moiety.

8. A packaging cell which expresses, at the cell surface,
   (i) a first mitogenic T-cell activating transmembrane protein which comprises a mitogenic domain which binds CD3 and a transmembrane domain; and
   (ii) a second mitogenic T cell activating transmembrane protein which comprises a mitogenic domain which binds CD28 and a transmembrane domain
   and comprises one or more of the following genes: gag, pol, env and/or rev.

9. A producer cell which expresses, at the cell surface,
   (i) a first mitogenic T-cell activating transmembrane protein which comprises a mitogenic domain which binds CD3 and a transmembrane domain; and/or
   (ii) a second mitogenic T cell activating transmembrane protein which comprises a mitogenic domain which binds CD28 and a transmembrane domain
   which comprises gag, pol, env and optionally rev genes and also comprises a retroviral or lentiviral genome.

10. A method for making a host cell according to claim 6, which comprises the step of transducing or transfecting a cell with a nucleic acid encoding a first mitogenic T-cell activating transmembrane protein and a second mitogenic T cell activating transmembrane protein.

11. A method for producing a viral vector according to claim 1 which comprises the step of expressing a retroviral or lentiviral genome in a cell.

12. A method for making an activated transgenic T-cell or natural killer (NK) cell, which comprises the step of transducing a T or NK cell with a viral vector according to claim 1, such that the T-cell or NK cell is activated by the one or more mitogenic T-cell activating transmembrane protein(s).

* * * * *

UNITED STATES PATENT AND TRADEMARK OFFICE
CERTIFICATE OF CORRECTION

PATENT NO. : 10,954,530 B2  
APPLICATION NO. : 15/554499  
DATED : March 23, 2021  
INVENTOR(S) : Martin Pulé et al.

Page 1 of 1

It is certified that error appears in the above-identified patent and that said Letters Patent is hereby corrected as shown below:

In the Claims

Column 61, Line 36, Claim 1 "domain" should be -- domain; --.

Column 61, Line 46, Claim 3 "domain" should be -- domain; --.

Column 62, Line 40, Claim 8 "domain" should be -- domain; --.

Column 62, Line 50, Claim 9 "domain" should be -- domain; --.

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*

```
                        SEQUENCE LISTING

<160> NUMBER OF SEQ ID NOS: 60

<210> SEQ ID NO 1
<211> LENGTH: 350
<212> TYPE: PRT
<213> ORGANISM: Artificial Sequence
<220> FEATURE:
<223> OTHER INFORMATION: Mitogenic T-cell activating transmembrane
      protein (OKT3-CD8STK-TM-A)

<400> SEQUENCE: 1

Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Ala Glu Leu Ala
            20                  25                  30

Arg Pro Gly Ala Ser Val Lys Met Ser Cys Lys Ala Ser Gly Tyr Thr
        35                  40                  45

Phe Thr Arg Tyr Thr Met His Trp Val Lys Gln Arg Pro Gly Gln Gly
    50                  55                  60

Leu Glu Trp Ile Gly Tyr Ile Asn Pro Ser Arg Gly Tyr Thr Asn Tyr
65                  70                  75                  80

Asn Gln Lys Phe Lys Asp Lys Ala Thr Leu Thr Thr Asp Lys Ser Ser
                85                  90                  95

Ser Thr Ala Tyr Met Gln Leu Ser Ser Leu Thr Ser Glu Asp Ser Ala
            100                 105                 110

Val Tyr Tyr Cys Ala Arg Tyr Tyr Asp Asp His Tyr Cys Leu Asp Tyr
        115                 120                 125

Trp Gly Gln Gly Thr Thr Leu Thr Val Ser Ser Gly Gly Gly Gly
    130                 135                 140

Ser Gly Gly Gly Gly Ser Gly Gly Gly Gly Ser Gln Ile Val Leu Thr
145                 150                 155                 160

Gln Ser Pro Ala Ile Met Ser Ala Ser Pro Gly Glu Lys Val Thr Met
                165                 170                 175
```

```
Thr Cys Ser Ala Ser Ser Ser Val Ser Tyr Met Asn Trp Tyr Gln Gln
                180                 185                 190

Lys Ser Gly Thr Ser Pro Lys Arg Trp Ile Tyr Asp Thr Ser Lys Leu
            195                 200                 205

Ala Ser Gly Val Pro Ala His Phe Arg Gly Ser Gly Ser Gly Thr Ser
        210                 215                 220

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                245                 250                 255

Lys Leu Glu Ile Asn Arg Ser Asp Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Asn His
                325                 330                 335

Arg Asn Arg Arg Arg Val Cys Lys Cys Pro Arg Pro Val Val
            340                 345                 350
```

<210> SEQ ID NO 2
<211> LENGTH: 358
<212> TYPE: PRT
<213> ORGANISM: Artificial Sequence
<220> FEATURE:
<223> OTHER INFORMATION: Mitogenic T-cell activating transmembrane
      protein (15E8-CD8STK-TM-A)

<400> SEQUENCE: 2

```
Met Glu Thr Asp Thr Leu Ile Leu Trp Val Leu Leu Leu Leu Val Pro
1               5                   10                  15

Gly Ser Thr Gly Gln Val Gln Leu Lys Glu Ser Gly Pro Gly Leu Val
            20                  25                  30

Ala Pro Ser Gln Ser Leu Ser Ile Thr Cys Thr Val Ser Gly Phe Ser
        35                  40                  45

Leu Thr Ser Tyr Gly Val His Trp Val Arg Gln Pro Pro Gly Lys Gly
    50                  55                  60

Leu Glu Trp Leu Gly Val Ile Trp Ala Gly Gly Ser Thr Asn Tyr Asn
65                  70                  75                  80

Ser Ala Leu Met Ser Arg Leu Ser Ile Ser Lys Asp Asn Ser Lys Ser
                85                  90                  95

Gln Val Phe Leu Lys Met Asn Ser Leu Gln Thr Asp Asp Thr Ala Met
            100                 105                 110

Tyr Tyr Cys Ala Arg Asp Lys Arg Ala Pro Gly Lys Leu Tyr Tyr Gly
        115                 120                 125

Tyr Pro Asp Tyr Trp Gly Gln Gly Thr Thr Leu Thr Val Ser Ser Gly
    130                 135                 140

Gly Gly Gly Ser Gly Gly Gly Gly Ser Gly Gly Gly Gly Ser Asp Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Glu Tyr Tyr Val Thr
            180                 185                 190
```

```
Ser Leu Met Gln Trp Tyr Gln Gln Lys Pro Gly Gln Pro Pro Lys Leu
            195                 200                 205

Leu Ile Tyr Ala Ala Ser Asn Val Glu Ser Gly Val Pro Ala Arg Phe
        210                 215                 220

Ser Gly Ser Gly Ser Gly Thr Asp Phe Ser Leu Asn Ile His Pro Val
225                 230                 235                 240

Glu Glu Asp Asp Ile Ala Met Tyr Phe Cys Gln Gln Thr Arg Lys Val
                245                 250                 255

Pro Ser Thr Phe Gly Gly Gly Thr Lys Leu Glu Ile Lys Arg Ser Asp
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn His Arg Asn Arg Arg Arg Val Cys Lys
            340                 345                 350

Cys Pro Arg Pro Val Val
            355

<210> SEQ ID NO 3
<211> LENGTH: 351
<212> TYPE: PRT
<213> ORGANISM: Artificial Sequence
<220> FEATURE:
<223> OTHER INFORMATION: Mitogenic T-cell activating transmembrane
      protein (TGN1412-CD8STK-TM-A)

<400> SEQUENCE: 3

Met Glu Thr Asp Thr Leu Ile Leu Trp Val Leu Leu Leu Leu Val Pro
1               5                   10                  15

Gly Ser Thr Gly Gln Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Ser Tyr Tyr Ile His Trp Val Arg Gln Ala Pro Gly Gln Gly
    50                  55                  60

Leu Glu Trp Ile Gly Cys Ile Tyr Pro Gly Asn Val Asn Thr Asn Tyr
65                  70                  75                  80

Asn Glu Lys Phe Lys Asp Arg Ala Thr Leu Thr Val Asp Thr Ser Ile
                85                  90                  95

Ser Thr Ala Tyr Met Glu Leu Ser Arg Leu Arg Ser Asp Asp Thr Ala
            100                 105                 110

Val Tyr Phe Cys Thr Arg Ser His Tyr Gly Leu Asp Trp Asn Phe Asp
        115                 120                 125

Val Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys His Ala Ser Gln Asn Ile Tyr Val Trp Leu Asn Trp Tyr Gln
            180                 185                 190
```

```
            Gln Lys Pro Gly Lys Ala Pro Lys Leu Leu Ile Tyr Lys Ala Ser Asn
                    195                 200                 205
        Leu His Thr Gly Val Pro Ser Arg Phe Ser Gly Ser Gly Ser Gly Thr
                210                 215                 220
        Asp Phe Thr Leu Thr Ile Ser Ser Leu Gln Pro Glu Asp Phe Ala Thr
        225                 230                 235                 240
        Tyr Tyr Cys Gln Gln Gly Gln Thr Tyr Pro Tyr Thr Phe Gly Gly Gly
                        245                 250                 255
        Thr Lys Val Glu Ile Lys Arg Ser Asp Pro Thr Thr Thr Pro Ala Pro
                        260                 265                 270
        Arg Pro Pro Thr Pro Ala Pro Thr Ile Ala Ser Gln Pro Leu Ser Leu
                    275                 280                 285
        Arg Pro Glu Ala Cys Arg Pro Ala Ala Gly Gly Ala Val His Thr Arg
                290                 295                 300
        Gly Leu Asp Phe Ala Cys Asp Ile Tyr Ile Trp Ala Pro Leu Ala Gly
        305                 310                 315                 320
        Thr Cys Gly Val Leu Leu Leu Ser Leu Val Ile Thr Leu Tyr Cys Asn
                        325                 330                 335
        His Arg Asn Arg Arg Arg Val Cys Lys Cys Pro Arg Pro Val Val
                        340                 345                 350

<210> SEQ ID NO 4
<211> LENGTH: 7
<212> TYPE: PRT
<213> ORGANISM: Artificial Sequence
<220> FEATURE:
<223> OTHER INFORMATION: OKT3 CDRH1

<400> SEQUENCE: 4

Gly Tyr Thr Phe Thr Arg Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: OKT3 CDRH2

<400> SEQUENCE: 5

Asn Pro Ser Arg Gly Tyr
1               5

<210> SEQ ID NO 6
<211> LENGTH: 10
<212> TYPE: PRT
<213> ORGANISM: Artificial Sequence
<220> FEATURE:
<223> OTHER INFORMATION: OKT3 CDRH3

<400> SEQUENCE: 6

Tyr Tyr Asp Asp His Tyr Cys Leu Asp Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: OKT3 CDRL1
```

```
<400> SEQUENCE: 7

Ser Ala Ser Ser Ser Val Ser Tyr Met Asn
1               5                   10

<210> SEQ ID NO 8
<211> LENGTH: 7
<212> TYPE: PRT
<213> ORGANISM: Artificial Sequence
<220> FEATURE:
<223> OTHER INFORMATION: OKT3 CDRL2

<400> SEQUENCE: 8

Asp Thr Ser Lys Leu Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: OKT3 CDRL3

<400> SEQUENCE: 9

Gln Gln Trp Ser Ser Asn Pro Phe Thr
1               5

<210> SEQ ID NO 10
<211> LENGTH: 7
<212> TYPE: PRT
<213> ORGANISM: Artificial Sequence
<220> FEATURE:
<223> OTHER INFORMATION: 15E8 CDRH1

<400> SEQUENCE: 10

Gly Phe Ser Leu Thr Ser Tyr
1               5

<210> SEQ ID NO 11
<211> LENGTH: 5
<212> TYPE: PRT
<213> ORGANISM: Artificial Sequence
<220> FEATURE:
<223> OTHER INFORMATION: 15E8 CDRH2

<400> SEQUENCE: 11

Trp Ala Gly Gly Ser
1               5

<210> SEQ ID NO 12
<211> LENGTH: 15
<212> TYPE: PRT
<213> ORGANISM: Artificial Sequence
<220> FEATURE:
<223> OTHER INFORMATION: 15E8 CDRH3

<400> SEQUENCE: 12

Asp Lys Arg Ala Pro Gly Lys Leu Tyr Tyr Gly Tyr Pro Asp Tyr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: 15E8 CDRL1
```

```
<400> SEQUENCE: 13

Arg Ala Ser Glu Ser Val Glu Tyr Tyr Val Thr Ser Leu Met Gln
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: 15E8 CDRL2

<400> SEQUENCE: 14

Ala Ala Ser Asn Val Glu Ser
1               5

<210> SEQ ID NO 15
<211> LENGTH: 9
<212> TYPE: PRT
<213> ORGANISM: Artificial Sequence
<220> FEATURE:
<223> OTHER INFORMATION: 15E8 CDRL3

<400> SEQUENCE: 15

Gln Gln Thr Arg Lys Val Pro Ser Thr
1               5

<210> SEQ ID NO 16
<211> LENGTH: 6
<212> TYPE: PRT
<213> ORGANISM: Artificial Sequence
<220> FEATURE:
<223> OTHER INFORMATION: TGN1412 CDRH1

<400> SEQUENCE: 16

Gly Tyr Thr Phe Ser Tyr
1               5

<210> SEQ ID NO 17
<211> LENGTH: 6
<212> TYPE: PRT
<213> ORGANISM: Artificial Sequence
<220> FEATURE:
<223> OTHER INFORMATION: TGN1412 CDRH2

<400> SEQUENCE: 17

Tyr Pro Gly Asn Val Asn
1               5

<210> SEQ ID NO 18
<211> LENGTH: 11
<212> TYPE: PRT
<213> ORGANISM: Artificial Sequence
<220> FEATURE:
<223> OTHER INFORMATION: TGN1412 CDRH3

<400> SEQUENCE: 18

Ser His Tyr Gly Leu Asp Trp Asn Phe Asp Val
1               5                   10

<210> SEQ ID NO 19
<211> LENGTH: 10
<212> TYPE: PRT
<213> ORGANISM: Artificial Sequence
<220> FEATURE:
<223> OTHER INFORMATION: TGN1412 CDRL1
```

```
<400> SEQUENCE: 19

His Ala Ser Gln Asn Ile Tyr Val Leu Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: TGN1412 CDRL2

<400> SEQUENCE: 20

Lys Ala Ser Asn Leu His Thr
1               5

<210> SEQ ID NO 21
<211> LENGTH: 9
<212> TYPE: PRT
<213> ORGANISM: Artificial Sequence
<220> FEATURE:
<223> OTHER INFORMATION: TGN1412 CDRL3

<400> SEQUENCE: 21

Gln Gln Gly Gln Thr Tyr Pro Tyr Thr
1               5

<210> SEQ ID NO 22
<211> LENGTH: 173
<212> TYPE: PRT
<213> ORGANISM: Artificial Sequence
<220> FEATURE:
<223> OTHER INFORMATION: OX40L sequence

<400> SEQUENCE: 22

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Tyr Leu Ile Ser Leu Lys
                85                  90                  95

Gly Tyr Phe Ser Gln Glu Val Asn Ile Ser Leu His Tyr Gln Lys Asp
            100                 105                 110

Glu Glu Pro Leu Phe Gln Leu Lys Lys Val Arg Ser Val Asn Ser Leu
        115                 120                 125

Met Val Ala Ser Leu Thr Tyr Lys Asp Lys Val Tyr Leu Asn Val Thr
    130                 135                 140

Thr Asp Asn Thr Ser Leu Asp Asp Phe His Val Asn Gly Gly Glu Leu
145                 150                 155                 160

Ile Leu Ile His Gln Asn Pro Gly Glu Phe Cys Val Leu
                165                 170

<210> SEQ ID NO 23
<211> LENGTH: 254
<212> TYPE: PRT
<213> ORGANISM: Artificial Sequence
```

```
<220> FEATURE:
<223> OTHER INFORMATION: 41BBL sequence

<400> SEQUENCE: 23

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Leu Ala Ala Cys Ala Val Phe
        35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 24
<211> LENGTH: 234
<212> TYPE: PRT
<213> ORGANISM: Artificial Sequence
<220> FEATURE:
<223> OTHER INFORMATION: spacer sequence, hinge-CH2CH3 of human IgG1

<400> SEQUENCE: 24

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
                20                  25                  30

Lys Asp Thr Leu Met Ile Ala Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80
```

```
Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 25
<211> LENGTH: 46
<212> TYPE: PRT
<213> ORGANISM: Artificial Sequence
<220> FEATURE:
<223> OTHER INFORMATION: spacer sequence, human CD8 stalk

<400> SEQUENCE: 25

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 26
<211> LENGTH: 20
<212> TYPE: PRT
<213> ORGANISM: Artificial Sequence
<220> FEATURE:
<223> OTHER INFORMATION: spacer sequence, human IgG1 hinge

<400> SEQUENCE: 26

Ala Glu Pro Lys Ser Pro Asp Lys Thr His Thr Cys Pro Pro Cys Pro
1               5                   10                  15

Lys Asp Pro Lys
            20

<210> SEQ ID NO 27
<211> LENGTH: 185
<212> TYPE: PRT
<213> ORGANISM: Artificial Sequence
<220> FEATURE:
<223> OTHER INFORMATION: spacer sequence, CD2 ectodomain
```

-continued

```
<400> SEQUENCE: 27

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
                20                  25                  30

Ile Lys Trp Glu Lys Thr Ser Asp Lys Lys Lys Ile Ala Gln Phe Arg
            35                  40                  45

Lys Glu Lys Glu Thr Phe Lys Glu Lys Asp Thr Tyr Lys Leu Phe Lys
        50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
        115                 120                 125

Asp Pro Glu Leu Asn Leu Tyr Gln Asp Gly Lys His Leu Lys Leu Ser
    130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185

<210> SEQ ID NO 28
<211> LENGTH: 259
<212> TYPE: PRT
<213> ORGANISM: Artificial Sequence
<220> FEATURE:
<223> OTHER INFORMATION: spacer sequence, CD34 ectodomain

<400> SEQUENCE: 28

Ser Leu Asp Asn Asn Gly Thr Ala Thr Pro Glu Leu Pro Thr Gln Gly
1               5                   10                  15

Thr Phe Ser Asn Val Ser Thr Asn Val Ser Tyr Gln Glu Thr Thr Thr
                20                  25                  30

Pro Ser Thr Leu Gly Ser Thr Ser Leu His Pro Val Ser Gln His Gly
            35                  40                  45

Asn Glu Ala Thr Thr Asn Ile Thr Glu Thr Thr Val Lys Phe Thr Ser
        50                  55                  60

Thr Ser Val Ile Thr Ser Val Tyr Gly Asn Thr Asn Ser Ser Val Gln
65                  70                  75                  80

Ser Gln Thr Ser Val Ile Ser Thr Val Phe Thr Thr Pro Ala Asn Val
                85                  90                  95

Ser Thr Pro Glu Thr Thr Leu Lys Pro Ser Leu Ser Pro Gly Asn Val
            100                 105                 110

Ser Asp Leu Ser Thr Thr Ser Thr Ser Leu Ala Thr Ser Pro Thr Lys
        115                 120                 125

Pro Tyr Thr Ser Ser Ser Pro Ile Leu Ser Asp Ile Lys Ala Glu Ile
    130                 135                 140

Lys Cys Ser Gly Ile Arg Glu Val Lys Leu Thr Gln Gly Ile Cys Leu
145                 150                 155                 160
```

```
Glu Gln Asn Lys Thr Ser Ser Cys Ala Glu Phe Lys Lys Asp Arg Gly
                165                 170                 175

Glu Gly Leu Ala Arg Val Leu Cys Gly Glu Gln Ala Asp Ala Asp
            180                 185                 190

Ala Gly Ala Gln Val Cys Ser Leu Leu Ala Gln Ser Glu Val Arg
        195                 200                 205

Pro Gln Cys Leu Leu Leu Val Leu Ala Asn Arg Thr Glu Ile Ser Ser
    210                 215                 220

Lys Leu Gln Leu Met Lys Lys His Gln Ser Asp Leu Lys Leu Gly
225                 230                 235                 240

Ile Leu Asp Phe Thr Glu Gln Asp Val Ala Ser His Gln Ser Tyr Ser
                245                 250                 255

Gln Lys Thr

<210> SEQ ID NO 29
<211> LENGTH: 153
<212> TYPE: PRT
<213> ORGANISM: Artificial Sequence
<220> FEATURE:
<223> OTHER INFORMATION: IL2 sequence

<400> SEQUENCE: 29

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 30
<211> LENGTH: 177
<212> TYPE: PRT
<213> ORGANISM: Artificial Sequence
<220> FEATURE:
<223> OTHER INFORMATION: IL7 sequence

<400> SEQUENCE: 30

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45
```

```
Leu Asp Ser Met Lys Glu Ile Gly Ser Asn Cys Leu Asn Asn Glu Phe
         50                  55                  60

Asn Phe Phe Lys Arg His Ile Cys Asp Ala Asn Lys Glu Gly Met Phe
 65                  70                  75                  80

Leu Phe Arg Ala Ala Arg Lys Leu Arg Gln Phe Leu Lys Met Asn Ser
                 85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
            115                 120                 125

Leu Gly Glu Ala Gln Pro Thr Lys Ser Leu Glu Glu Asn Lys Ser Leu
130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

```
<210> SEQ ID NO 31
<211> LENGTH: 162
<212> TYPE: PRT
<213> ORGANISM: Artificial Sequence
<220> FEATURE:
<223> OTHER INFORMATION: IL15 sequence

<400> SEQUENCE: 31

Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
                 20                  25                  30

Val Phe Ile Leu Gly Cys Phe Ser Ala Gly Leu Pro Lys Thr Glu Ala
             35                  40                  45

Asn Trp Val Asn Val Ile Ser Asp Leu Lys Lys Ile Glu Asp Leu Ile
 50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser
```

```
<210> SEQ ID NO 32
<211> LENGTH: 271
<212> TYPE: PRT
<213> ORGANISM: Artificial Sequence
<220> FEATURE:
<223> OTHER INFORMATION: cytokine-based T-cell activating transmembrane
      protein sequence
```

<400> SEQUENCE: 32

Met Ala His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His Ser Gly Gly Gly Ser Pro Ala Lys Pro Thr Thr Thr Pro Ala Pro
            180                 185                 190

Arg Pro Pro Thr Pro Ala Pro Thr Ile Ala Ser Gln Pro Leu Ser Leu
        195                 200                 205

Arg Pro Glu Ala Cys Arg Pro Ala Ala Gly Gly Ala Val His Thr Arg
    210                 215                 220

Gly Leu Asp Phe Ala Cys Asp Ile Tyr Ile Trp Ala Pro Leu Ala Gly
225                 230                 235                 240

Thr Cys Gly Val Leu Leu Leu Ser Leu Val Ile Thr Leu Tyr Cys Asn
                245                 250                 255

His Arg Asn Arg Arg Val Cys Lys Cys Pro Arg Pro Val Val
            260                 265                 270

<210> SEQ ID NO 33
<211> LENGTH: 256
<212> TYPE: PRT
<213> ORGANISM: Artificial Sequence
<220> FEATURE:
<223> OTHER INFORMATION: cytokine-based T-cell activating transmembrane
      protein sequence

<400> SEQUENCE: 33

Met Gly Leu Val Arg Arg Gly Ala Arg Ala Gly Pro Arg Met Pro Arg
1               5                   10                  15

Gly Trp Thr Ala Leu Cys Leu Leu Ser Leu Leu Pro Ser Gly Phe Met
            20                  25                  30

Ala Gly Ile His Val Phe Ile Leu Gly Cys Phe Ser Ala Gly Leu Pro
        35                  40                  45

Lys Thr Glu Ala Asn Trp Val Asn Val Ile Ser Asp Leu Lys Lys Ile
    50                  55                  60

Glu Asp Leu Ile Gln Ser Met His Ile Asp Ala Thr Leu Tyr Thr Glu
65                  70                  75                  80

```
Ser Asp Val His Pro Ser Cys Lys Val Thr Ala Met Lys Cys Phe Leu
                85                  90                  95

Leu Glu Leu Gln Val Ile Ser Leu Glu Ser Gly Asp Ala Ser Ile His
            100                 105                 110

Asp Thr Val Glu Asn Leu Ile Ile Leu Ala Asn Asn Ser Leu Ser Ser
        115                 120                 125

Asn Gly Asn Val Thr Glu Ser Gly Cys Lys Glu Cys Glu Glu Leu Glu
130                 135                 140

Glu Lys Asn Ile Lys Glu Phe Leu Gln Ser Phe Val His Ile Val Gln
145                 150                 155                 160

Met Phe Ile Asn Thr Ser Ser Pro Ala Lys Pro Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240

Asn His Arg Asn Arg Arg Arg Val Cys Lys Cys Pro Arg Pro Val Val
                245                 250                 255

<210> SEQ ID NO 34
<211> LENGTH: 20
<212> TYPE: PRT
<213> ORGANISM: Artificial Sequence
<220> FEATURE:
<223> OTHER INFORMATION: self-cleaving site

<400> SEQUENCE: 34

Arg Ala Glu Gly Arg Gly Ser Leu Leu Thr Cys Gly Asp Val Glu Glu
1               5                   10                  15

Asn Pro Gly Pro
            20

<210> SEQ ID NO 35
<211> LENGTH: 20
<212> TYPE: PRT
<213> ORGANISM: Artificial Sequence
<220> FEATURE:
<223> OTHER INFORMATION: self-cleaving site

<400> SEQUENCE: 35

Gln Cys Thr Asn Tyr Ala Leu Leu Lys Leu Ala Gly Asp Val Glu Ser
1               5                   10                  15

Asn Pro Gly Pro
            20

<210> SEQ ID NO 36
<211> LENGTH: 8
<212> TYPE: PRT
<213> ORGANISM: Artificial Sequence
<220> FEATURE:
<223> OTHER INFORMATION: biotin mimic, streptagII

<400> SEQUENCE: 36

Trp Ser His Pro Gln Phe Glu Lys
1               5
```

```
<210> SEQ ID NO 37
<211> LENGTH: 15
<212> TYPE: PRT
<213> ORGANISM: Artificial Sequence
<220> FEATURE:
<223> OTHER INFORMATION: biotin mimic, flankedccstreptag

<400> SEQUENCE: 37

Ala Glu Cys His Pro Gln Gly Pro Pro Cys Ile Glu Gly Arg Lys
1               5                   10                  15

<210> SEQ ID NO 38
<211> LENGTH: 8
<212> TYPE: PRT
<213> ORGANISM: Artificial Sequence
<220> FEATURE:
<223> OTHER INFORMATION: biotin mimic, ccstreptag

<400> SEQUENCE: 38

Cys His Pro Gln Gly Pro Pro Cys
1               5

<210> SEQ ID NO 39
<211> LENGTH: 15
<212> TYPE: PRT
<213> ORGANISM: Artificial Sequence
<220> FEATURE:
<223> OTHER INFORMATION: biotin mimic, Long nanotag

<400> SEQUENCE: 39

Asp Val Glu Ala Trp Leu Asp Glu Arg Val Pro Leu Val Glu Thr
1               5                   10                  15

<210> SEQ ID NO 40
<211> LENGTH: 9
<212> TYPE: PRT
<213> ORGANISM: Artificial Sequence
<220> FEATURE:
<223> OTHER INFORMATION: biotin mimic, Short nanotag

<400> SEQUENCE: 40

Asp Val Glu Ala Trp Leu Gly Ala Arg
1               5

<210> SEQ ID NO 41
<211> LENGTH: 8
<212> TYPE: PRT
<213> ORGANISM: Artificial Sequence
<220> FEATURE:
<223> OTHER INFORMATION: biotin mimic, Streptag

<400> SEQUENCE: 41

Trp Arg His Pro Gln Phe Gly Gly
1               5

<210> SEQ ID NO 42
<211> LENGTH: 38
<212> TYPE: PRT
<213> ORGANISM: Artificial Sequence
<220> FEATURE:
<223> OTHER INFORMATION: biotin mimic, SBP-tag
```

-continued

```
<400> SEQUENCE: 42

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 43
<211> LENGTH: 36
<212> TYPE: PRT
<213> ORGANISM: Artificial Sequence
<220> FEATURE:
<223> OTHER INFORMATION: binding domain, StreptagII-d8-x2

<400> SEQUENCE: 43

Trp Ser His Pro Gln Phe Glu Lys Ser Gly Gly Gly Ser Pro Ala
1               5                   10                  15

Pro Arg Pro Pro Thr Pro Ala Pro Thr Ile Ala Ser Trp Ser His Pro
            20                  25                  30

Gln Phe Glu Lys
        35

<210> SEQ ID NO 44
<211> LENGTH: 50
<212> TYPE: PRT
<213> ORGANISM: Artificial Sequence
<220> FEATURE:
<223> OTHER INFORMATION: binding domain, Flankedccstreptag-d8-x2

<400> SEQUENCE: 44

Glu Cys His Pro Gln Gly Pro Pro Cys Ile Glu Gly Arg Lys Ser Ser
1               5                   10                  15

Gly Gly Gly Gly Ser Pro Ala Pro Arg Pro Pro Thr Pro Ala Pro Thr
            20                  25                  30

Ile Ala Ser Glu Cys His Pro Gln Gly Pro Pro Cys Ile Glu Gly Arg
        35                  40                  45

Lys Ser
    50

<210> SEQ ID NO 45
<211> LENGTH: 251
<212> TYPE: PRT
<213> ORGANISM: Artificial Sequence
<220> FEATURE:
<223> OTHER INFORMATION: glutathione S-transferase (GST) domain

<400> SEQUENCE: 45

Met Gly Thr Ser Leu Leu Cys Trp Met Ala Leu Cys Leu Leu Gly Ala
1               5                   10                  15

Asp His Ala Asp Ala Met Ser Pro Ile Leu Gly Tyr Trp Lys Ile Lys
            20                  25                  30

Gly Leu Val Gln Pro Thr Arg Leu Leu Leu Glu Tyr Leu Glu Glu Lys
        35                  40                  45

Tyr Glu Glu His Leu Tyr Glu Arg Asp Glu Gly Asp Lys Trp Arg Asn
    50                  55                  60

Lys Lys Phe Glu Leu Gly Leu Glu Phe Pro Asn Leu Pro Tyr Tyr Ile
65                  70                  75                  80

Asp Gly Asp Val Lys Leu Thr Gln Ser Met Ala Ile Ile Arg Tyr Ile
            85                  90                  95
```

-continued

```
Ala Asp Lys His Asn Met Leu Gly Gly Cys Pro Lys Glu Arg Ala Glu
            100                 105                 110

Ile Ser Met Leu Glu Gly Ala Val Leu Asp Ile Arg Tyr Gly Val Ser
        115                 120                 125

Arg Ile Ala Tyr Ser Lys Asp Phe Glu Thr Leu Lys Val Asp Phe Leu
    130                 135                 140

Ser Lys Leu Pro Glu Met Leu Lys Met Phe Glu Asp Arg Leu Cys His
145                 150                 155                 160

Lys Thr Tyr Leu Asn Gly Asp His Val Thr His Pro Asp Phe Met Leu
                165                 170                 175

Tyr Asp Ala Leu Asp Val Val Leu Tyr Met Asp Pro Met Cys Leu Asp
            180                 185                 190

Ala Phe Pro Lys Leu Val Cys Phe Lys Lys Arg Ile Glu Ala Ile Pro
        195                 200                 205

Gln Ile Asp Lys Tyr Leu Lys Ser Ser Lys Tyr Ile Ala Trp Pro Leu
    210                 215                 220

Gln Gly Trp Gln Ala Thr Phe Gly Gly Asp His Pro Pro Lys Ser
225                 230                 235                 240

Asp Leu Glu Val Leu Phe Gln Gly Pro Leu Gly
                245                 250

<210> SEQ ID NO 46
<211> LENGTH: 17
<212> TYPE: PRT
<213> ORGANISM: Artificial Sequence
<220> FEATURE:
<223> OTHER INFORMATION: Rituximab-binding epitope sequence from CD20

<400> SEQUENCE: 46

Cys Glu Pro Ala Asn Pro Ser Glu Lys Asn Ser Pro Ser Thr Gln Tyr
1               5                   10                  15

Cys

<210> SEQ ID NO 47
<211> LENGTH: 10
<212> TYPE: PRT
<213> ORGANISM: Artificial Sequence
<220> FEATURE:
<223> OTHER INFORMATION: cysteine-constrained 7-mer cyclic peptide,
      R15-C

<400> SEQUENCE: 47

Ala Cys Pro Tyr Ala Asn Pro Ser Leu Cys
1               5                   10

<210> SEQ ID NO 48
<211> LENGTH: 10
<212> TYPE: PRT
<213> ORGANISM: Artificial Sequence
<220> FEATURE:
<223> OTHER INFORMATION: cysteine-constrained 7-mer cyclic peptide, R3-C

<400> SEQUENCE: 48

Ala Cys Pro Tyr Ser Asn Pro Ser Leu Cys
1               5                   10

<210> SEQ ID NO 49
<211> LENGTH: 10
<212> TYPE: PRT
<213> ORGANISM: Artificial Sequence
<220> FEATURE:
<223> OTHER INFORMATION: cysteine-constrained 7-mer cyclic peptide, R7-C
```

-continued

```
<400> SEQUENCE: 49

Ala Cys Pro Phe Ala Asn Pro Ser Thr Cys
1               5                   10

<210> SEQ ID NO 50
<211> LENGTH: 10
<212> TYPE: PRT
<213> ORGANISM: Artificial Sequence
<220> FEATURE:
<223> OTHER INFORMATION: cysteine-constrained 7-mer cyclic peptide, R8-,
      R12-, R18-C

<400> SEQUENCE: 50

Ala Cys Asn Phe Ser Asn Pro Ser Leu Cys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: cysteine-constrained 7-mer cyclic peptide,
      R14-C

<400> SEQUENCE: 51

Ala Cys Pro Phe Ser Asn Pro Ser Met Cys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: cysteine-constrained 7-mer cyclic peptide,
      R16-C

<400> SEQUENCE: 52

Ala Cys Ser Trp Ala Asn Pro Ser Gln Cys
1               5                   10

<210> SEQ ID NO 53
<211> LENGTH: 10
<212> TYPE: PRT
<213> ORGANISM: Artificial Sequence
<220> FEATURE:
<223> OTHER INFORMATION: cysteine-constrained 7-mer cyclic peptide,
      R17-C

<400> SEQUENCE: 53

Ala Cys Met Phe Ser Asn Pro Ser Leu Cys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: cysteine-constrained 7-mer cyclic peptide,
      R19-C

<400> SEQUENCE: 54

Ala Cys Pro Phe Ala Asn Pro Ser Met Cys
1               5                   10
```

```
<210> SEQ ID NO 55
<211> LENGTH: 10
<212> TYPE: PRT
<213> ORGANISM: Artificial Sequence
<220> FEATURE:
<223> OTHER INFORMATION: cysteine-constrained 7-mer cyclic peptide,
      R2-C

<400> SEQUENCE: 55

Ala Cys Trp Ala Ser Asn Pro Ser Leu Cys
1               5                   10

<210> SEQ ID NO 56
<211> LENGTH: 10
<212> TYPE: PRT
<213> ORGANISM: Artificial Sequence
<220> FEATURE:
<223> OTHER INFORMATION: cysteine-constrained 7-mer cyclic peptide,
      R10-C

<400> SEQUENCE: 56

Ala Cys Glu His Ser Asn Pro Ser Leu Cys
1               5                   10

<210> SEQ ID NO 57
<211> LENGTH: 10
<212> TYPE: PRT
<213> ORGANISM: Artificial Sequence
<220> FEATURE:
<223> OTHER INFORMATION: cysteine-constrained 7-mer cyclic peptide,
      R13-C

<400> SEQUENCE: 57

Ala Cys Trp Ala Ala Asn Pro Ser Met Cys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: mimetope of Rituximab

<400> SEQUENCE: 58

Gln Asp Lys Leu Thr Gln Trp Pro Lys Trp Leu Glu
1               5                   10

<210> SEQ ID NO 59
<211> LENGTH: 16
<212> TYPE: PRT
<213> ORGANISM: Artificial Sequence
<220> FEATURE:
<223> OTHER INFORMATION: QBEnd10-binding epitope from within the CD34
      antigen

<400> SEQUENCE: 59

Glu Leu Pro Thr Gln Gly Thr Phe Ser Asn Val Ser Thr Asn Val Ser
1               5                   10                  15

<210> SEQ ID NO 60
<211> LENGTH: 136
<212> TYPE: PRT
<213> ORGANISM: Artificial Sequence
<220> FEATURE:
<223> OTHER INFORMATION: binding domain RQR8
```

```
<400> SEQUENCE: 60

Cys Pro Tyr Ser Asn Pro Ser Leu Cys Ser Gly Gly Gly Ser Glu
1               5                   10                  15

Leu Pro Thr Gln Gly Thr Phe Ser Asn Val Ser Thr Asn Val Ser Pro
            20                  25                  30

Ala Lys Pro Thr Thr Thr Ala Cys Pro Tyr Ser Asn Pro Ser Leu Cys
        35                  40                  45

Ser Gly Gly Gly Ser Pro Ala Pro Arg Pro Pro Thr Pro Ala Pro
    50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
            100                 105                 110

Ser Leu Val Ile Thr Leu Tyr Cys Asn His Arg Asn Arg Arg Arg Val
            115                 120                 125

Cys Lys Cys Pro Arg Pro Val Val
130                 135
```